US011363966B2

(12) United States Patent
Kusens et al.

(10) Patent No.: US 11,363,966 B2
(45) Date of Patent: *Jun. 21, 2022

(54) DETECTING UNAUTHORIZED VISITORS

(71) Applicant: CERNER INNOVATION, INC., Kansas City, KS (US)

(72) Inventors: Michael Kusens, Cooper City, FL (US); Neil Kusens, Sherman Oaks, CA (US)

(73) Assignee: CERNER INNOVATION, INC., North Kansas City, MO (US)

(*) Notice: Subject to any disclaimer, the term of this patent is extended or adjusted under 35 U.S.C. 154(b) by 105 days.

This patent is subject to a terminal disclaimer.

(21) Appl. No.: 16/830,498

(22) Filed: Mar. 26, 2020

(65) Prior Publication Data

US 2020/0226353 A1 Jul. 16, 2020

Related U.S. Application Data

(63) Continuation of application No. 16/454,508, filed on Jun. 27, 2019, now Pat. No. 10,643,061, which is a (Continued)

(51) Int. Cl.
*G06K 9/00* (2022.01)
*H04N 7/18* (2006.01)
(Continued)

(52) U.S. Cl.
CPC ............. *A61B 5/11* (2013.01); *A61B 5/0077* (2013.01); *A61B 5/1176* (2013.01);
(Continued)

(58) Field of Classification Search
USPC ........ 382/100, 103, 106–107, 128–133, 154, 382/155, 162, 168, 173, 181, 190, 199, (Continued)

(56) References Cited

U.S. PATENT DOCUMENTS 4,669,263 A 6/1987 Sugiyama
4,857,716 A 8/1989 Gombrich et al.
(Continued)

FOREIGN PATENT DOCUMENTS

DE 19844918 A1 4/2000
WO 2007/081629 A2 7/2007
(Continued)

OTHER PUBLICATIONS

Pre-Interview First Office action received for U.S. Appl. No. 16/816,626, dated Dec. 22, 2020, 4 pages.
(Continued)

*Primary Examiner* — Seyed H Azarian
(74) *Attorney, Agent, or Firm* — Shook, Hardy & Bacon LLP

(57) ABSTRACT

An unauthorized visitor system collects an image of a person detected in a room of a patient. The system identifies reference points on the person's face, for example, points along the cheeks, jowls, and/or brow. The system may compare the reference points to reference points of images associated with registered visitors. The system then determines, based on the comparison, if the person is a registered visitor. One or more designated recipients may be alerted if the person is not a registered visitor or if the person breaches a patient identification zone established around a particular patient. The system may also register the person in a database of visitors.

20 Claims, 19 Drawing Sheets

Related U.S. Application Data continuation of application No. 16/216,210, filed on Dec. 11, 2018, now Pat. No. 10,410,042, which is a continuation of application No. 15/848,621, filed on Dec. 20, 2017, now Pat. No. 10,210,378, which is a continuation of application No. 15/395,526, filed on Dec. 30, 2016, now Pat. No. 9,892,311.

(60) Provisional application No. 62/273,735, filed on Dec. 31, 2015.

(51) Int. Cl.

| | | |
|---|---|---|
| *A61B 5/11* | (2006.01) | |
| *G08B 5/22* | (2006.01) | |
| *G08B 25/00* | (2006.01) | |
| *G08B 21/18* | (2006.01) | |
| *G06T 7/292* | (2017.01) | |
| *G06T 7/20* | (2017.01) | |
| *G16H 40/63* | (2018.01) | |
| *G16H 10/60* | (2018.01) | |
| *H04N 13/204* | (2018.01) | |
| *H04N 13/207* | (2018.01) | |
| *G16H 40/20* | (2018.01) | |
| *G06V 10/42* | (2022.01) | |
| *G06V 10/44* | (2022.01) | |
| *G06V 20/52* | (2022.01) | |
| *G06V 20/64* | (2022.01) | |
| *G06V 40/20* | (2022.01) | |
| *G06V 40/16* | (2022.01) | |
| *A61B 5/00* | (2006.01) | |
| *G06K 9/62* | (2022.01) | |
| *G06T 7/00* | (2017.01) | |
| *G06T 11/60* | (2006.01) | |
| *H04N 5/232* | (2006.01) | |
| *A61B 5/1171* | (2016.01) | |
| *G08B 13/196* | (2006.01) | |
| *G16H 30/20* | (2018.01) | |
| *G16H 15/00* | (2018.01) | |
| *G16H 80/00* | (2018.01) | |
| *G16H 40/67* | (2018.01) | |
| *G16H 50/30* | (2018.01) | |
| *G16H 20/10* | (2018.01) | |
| *G08B 21/04* | (2006.01) | |
| *H04N 13/00* | (2018.01) | |
| *G06F 3/0482* | (2013.01) | |
| *G06F 3/04847* | (2022.01) | |

(52) U.S. Cl.
CPC .......... *A61B 5/4064* (2013.01); *A61B 5/746* (2013.01); *G06K 9/6215* (2013.01); *G06T 7/0012* (2013.01); *G06T 7/0016* (2013.01); *G06T 7/20* (2013.01); *G06T 7/292* (2017.01); *G06T 11/60* (2013.01); *G06V 10/42* (2022.01); *G06V 10/44* (2022.01); *G06V 20/52* (2022.01); *G06V 20/647* (2022.01); *G06V 40/172* (2022.01); *G06V 40/20* (2022.01); *G08B 5/22* (2013.01); *G08B 13/196* (2013.01); *G08B 21/182* (2013.01); *G08B 25/009* (2013.01); *G16H 10/60* (2018.01); *G16H 15/00* (2018.01); *G16H 20/10* (2018.01); *G16H 30/20* (2018.01); *G16H 40/20* (2018.01); *G16H 40/63* (2018.01); *G16H 40/67* (2018.01); *G16H 50/30* (2018.01); *G16H 80/00* (2018.01); *H04N 5/23293* (2013.01); *H04N 7/18* (2013.01); *H04N 7/181* (2013.01); *H04N 7/183* (2013.01); *H04N 13/204* (2018.05); *H04N 13/207* (2018.05); *G06F 3/0482* (2013.01); *G06F 3/04847* (2013.01); *G06T 2200/04* (2013.01); *G06T 2200/24* (2013.01); *G06T 2207/10012* (2013.01); *G06T 2207/10021* (2013.01); *G06T 2207/10024* (2013.01); *G06T 2207/20221* (2013.01); *G06T 2207/30201* (2013.01); *G06T 2207/30232* (2013.01); *G06V 40/161* (2022.01); *G08B 13/19639* (2013.01); *G08B 21/0476* (2013.01); *H04N 2013/0085* (2013.01)

(58) Field of Classification Search
USPC ....... 382/203, 209, 214, 219, 232, 254, 274, 382/276, 286–291, 305, 312; 128/4, 21, 128/903; 348/539.12, 143; 600/476
See application file for complete search history.

(56) References Cited

U.S. PATENT DOCUMENTS

| | | |
|---|---|---|
| 5,031,228 A | 7/1991 | Lu |
| 5,276,432 A | 1/1994 | Travis |
| 5,448,221 A | 9/1995 | Weller |
| 5,482,050 A | 1/1996 | Smokoff et al. |
| 5,592,153 A | 1/1997 | Welling et al. |
| 5,798,798 A | 8/1998 | Rector et al. |
| 5,838,223 A | 11/1998 | Gallant et al. |
| 5,915,379 A | 6/1999 | Wallace et al. |
| 5,942,986 A | 8/1999 | Shabot et al. |
| 6,050,940 A | 4/2000 | Braun et al. |
| 6,095,984 A | 8/2000 | Amano et al. |
| 6,160,478 A * | 12/2000 | Jacobsen .............. A61B 5/6838 128/903 |
| 6,174,283 B1 | 1/2001 | Nevo et al. |
| 6,188,407 B1 | 2/2001 | Smith et al. |
| 6,269,812 B1 | 8/2001 | Wallace et al. |
| 6,287,452 B1 | 9/2001 | Allen et al. |
| 6,322,502 B1 | 11/2001 | Schoenberg et al. |
| 6,369,838 B1 | 4/2002 | Wallace et al. |
| 6,429,869 B1 | 8/2002 | Kamakura et al. |
| 6,614,349 B1 | 9/2003 | Proctor et al. |
| 6,727,818 B1 | 4/2004 | Wildman et al. |
| 6,804,656 B1 | 10/2004 | Rosenfeld et al. |
| 7,015,816 B2 | 3/2006 | Wildman et al. |
| 7,122,005 B2 | 10/2006 | Shusterman |
| 7,154,397 B2 | 12/2006 | Zerhusen et al. |
| 7,237,287 B2 | 7/2007 | Weismiller et al. |
| 7,323,991 B1 | 1/2008 | Eckert et al. |
| 7,408,470 B2 | 8/2008 | Wildman et al. |
| 7,420,472 B2 | 9/2008 | Tran |
| 7,430,608 B2 | 9/2008 | Noonan et al. |
| 7,502,498 B2 | 3/2009 | Wen et al. |
| 7,612,679 B1 | 11/2009 | Fackler et al. |
| 7,669,263 B2 | 3/2010 | Menkedick et al. |
| 7,715,387 B2 | 5/2010 | Schuman |
| 7,724,147 B2 | 5/2010 | Brown |
| 7,756,723 B2 | 7/2010 | Rosow et al. |
| 7,890,349 B2 | 2/2011 | Cole et al. |
| 7,893,842 B2 | 2/2011 | Deutsch |
| 7,895,055 B2 | 2/2011 | Schneider et al. |
| 7,908,153 B2 | 3/2011 | Scherpbier et al. |
| 7,945,457 B2 | 5/2011 | Zaleski |
| 7,962,544 B2 | 6/2011 | Torok et al. |
| 7,972,140 B2 | 7/2011 | Renaud |
| 8,108,036 B2 | 1/2012 | Tran |
| 8,123,685 B2 | 2/2012 | Brauers et al. |
| 8,128,596 B2 | 3/2012 | Carter |
| 8,190,447 B2 | 5/2012 | Hungerford et al. |
| 8,224,108 B2 | 7/2012 | Steinberg et al. |
| 8,237,558 B2 | 8/2012 | Seyed Momen et al. |
| 8,273,018 B1 | 9/2012 | Fackler et al. |
| 8,432,263 B2 | 4/2013 | Kunz |
| 8,451,314 B1 | 5/2013 | Cline et al. |
| 8,529,448 B2 | 9/2013 | McNair |

(56) References Cited

U.S. PATENT DOCUMENTS

| | | |
|---|---|---|
| 8,565,500 B2 | 10/2013 | Neff |
| 8,620,682 B2 | 12/2013 | Bechtel et al. |
| 8,655,680 B2 | 2/2014 | Bechtel et al. |
| 8,700,423 B2 | 4/2014 | Eaton, Jr. et al. |
| 8,727,981 B2 | 5/2014 | Bechtel et al. |
| 8,769,153 B2 | 7/2014 | Dziubinski |
| 8,890,937 B2 | 11/2014 | Skubic et al. |
| 8,902,068 B2 | 12/2014 | Bechtel et al. |
| 8,917,186 B1 | 12/2014 | Grant |
| 8,953,886 B2 | 2/2015 | King et al. |
| 9,072,929 B1 | 7/2015 | Rush et al. |
| 9,129,506 B1 | 9/2015 | Kusens |
| 9,147,334 B2 | 9/2015 | Long et al. |
| 9,159,215 B1 * | 10/2015 | Kusens ............... A61B 5/1115 |
| 9,269,012 B2 | 2/2016 | Fotland |
| 9,292,089 B1 | 3/2016 | Sadek |
| 9,305,191 B2 | 4/2016 | Long et al. |
| 9,367,270 B1 | 6/2016 | Robertson |
| 9,408,561 B2 | 8/2016 | Stone et al. |
| 9,489,820 B1 | 11/2016 | Kusens |
| 9,519,969 B1 | 12/2016 | Kusens |
| 9,524,443 B1 | 12/2016 | Kusens |
| 9,536,310 B1 | 1/2017 | Kusens |
| 9,538,158 B1 | 1/2017 | Rush et al. |
| 9,563,955 B1 | 2/2017 | Kamarshi et al. |
| 9,597,016 B2 | 3/2017 | Stone et al. |
| 9,729,833 B1 | 8/2017 | Kusens |
| 9,741,227 B1 | 8/2017 | Kusens |
| 9,892,310 B2 | 2/2018 | Kusens et al. |
| 9,892,311 B2 | 2/2018 | Kusens et al. |
| 9,892,611 B1 | 2/2018 | Kusens |
| 9,905,113 B2 | 2/2018 | Kusens |
| 9,934,427 B2 | 4/2018 | Derenne et al. |
| 10,078,956 B1 | 9/2018 | Kusens |
| 10,090,068 B2 | 10/2018 | Kusens et al. |
| 10,091,463 B1 | 10/2018 | Kusens |
| 10,096,223 B1 | 10/2018 | Kusens |
| 10,210,378 B2 | 2/2019 | Kusens et al. |
| 10,225,522 B1 | 3/2019 | Kusens |
| 10,342,478 B2 | 7/2019 | Kusens |
| 10,524,722 B2 | 1/2020 | Kusens et al. |
| 10,643,446 B2 | 5/2020 | Kusens et al. |
| 10,878,220 B2 | 12/2020 | Kusens |
| 10,922,946 B2 | 2/2021 | Kusens et al. |
| 2002/0015034 A1 | 2/2002 | Malmborg |
| 2002/0038073 A1 | 3/2002 | August |
| 2002/0077863 A1 | 6/2002 | Rutledge et al. |
| 2002/0101349 A1 | 8/2002 | Rojas, Jr. |
| 2002/0115905 A1 | 8/2002 | August |
| 2002/0183976 A1 | 12/2002 | Pearce |
| 2003/0037786 A1 | 2/2003 | Biondi et al. |
| 2003/0070177 A1 | 4/2003 | Kondo et al. |
| 2003/0092974 A1 | 5/2003 | Santoso et al. |
| 2003/0095147 A1 | 5/2003 | Daw |
| 2003/0135390 A1 | 7/2003 | O'Brien et al. |
| 2003/0140928 A1 | 7/2003 | Bui et al. |
| 2003/0227386 A1 | 12/2003 | Pulkkinen et al. |
| 2004/0019900 A1 | 1/2004 | Knightbridge et al. |
| 2004/0052418 A1 | 3/2004 | DeLean |
| 2004/0054760 A1 | 3/2004 | Ewing et al. |
| 2004/0097227 A1 | 5/2004 | Siegel |
| 2004/0116804 A1 | 6/2004 | Mostafavi |
| 2004/0193449 A1 | 9/2004 | Wildman et al. |
| 2005/0038326 A1 | 2/2005 | Mathur |
| 2005/0182305 A1 | 8/2005 | Hendrich |
| 2005/0231341 A1 | 10/2005 | Shimizu |
| 2005/0249139 A1 | 11/2005 | Nesbit |
| 2006/0004606 A1 | 1/2006 | Wendl et al. |
| 2006/0047538 A1 | 3/2006 | Condurso et al. |
| 2006/0049936 A1 | 3/2006 | Collins et al. |
| 2006/0058587 A1 | 3/2006 | Heimbrock et al. |
| 2006/0089541 A1 | 4/2006 | Braun et al. |
| 2006/0092043 A1 | 5/2006 | Lagassey |
| 2006/0107295 A1 | 5/2006 | Margis et al. |
| 2006/0145874 A1 | 7/2006 | Fredriksson et al. |
| 2006/0261974 A1 | 11/2006 | Albert et al. |
| 2007/0033072 A1 | 2/2007 | Bildirici |
| 2007/0083445 A1 | 4/2007 | Garcia et al. |
| 2007/0085690 A1 | 4/2007 | Tran |
| 2007/0118054 A1 | 5/2007 | Pinhas et al. |
| 2007/0120689 A1 | 5/2007 | Zerhusen et al. |
| 2007/0129983 A1 | 6/2007 | Scherpbier et al. |
| 2007/0136102 A1 | 6/2007 | Rodgers |
| 2007/0136218 A1 | 6/2007 | Bauer et al. |
| 2007/0159332 A1 | 7/2007 | Koblasz |
| 2007/0279219 A1 | 12/2007 | Warriner |
| 2007/0296600 A1 | 12/2007 | Dixon et al. |
| 2008/0001735 A1 | 1/2008 | Tran |
| 2008/0001763 A1 | 1/2008 | Raja et al. |
| 2008/0002860 A1 | 1/2008 | Super et al. |
| 2008/0004904 A1 | 1/2008 | Tran |
| 2008/0009686 A1 | 1/2008 | Hendrich |
| 2008/0015903 A1 | 1/2008 | Rodgers |
| 2008/0021731 A1 | 1/2008 | Rodgers |
| 2008/0071210 A1 | 3/2008 | Moubayed et al. |
| 2008/0087719 A1 | 4/2008 | Sahud |
| 2008/0106374 A1 | 5/2008 | Sharbaugh |
| 2008/0126132 A1 | 5/2008 | Warner et al. |
| 2008/0228045 A1 | 9/2008 | Gao et al. |
| 2008/0249376 A1 | 10/2008 | Zaleski |
| 2008/0267447 A1 | 10/2008 | Kelusky et al. |
| 2008/0277486 A1 | 11/2008 | Seem et al. |
| 2008/0281638 A1 | 11/2008 | Weatherly et al. |
| 2009/0082829 A1 | 3/2009 | Panken et al. |
| 2009/0091458 A1 | 4/2009 | Deutsch |
| 2009/0099480 A1 | 4/2009 | Salgo et al. |
| 2009/0112630 A1 | 4/2009 | Collins et al. |
| 2009/0119843 A1 | 5/2009 | Rodgers et al. |
| 2009/0177327 A1 | 7/2009 | Turner et al. |
| 2009/0224924 A1 | 9/2009 | Thorp |
| 2009/0278934 A1 | 11/2009 | Ecker et al. |
| 2009/0322513 A1 | 12/2009 | Hwang et al. |
| 2009/0326340 A1 | 12/2009 | Wang et al. |
| 2010/0117836 A1 | 5/2010 | Seyed Momen et al. |
| 2010/0169114 A1 | 7/2010 | Henderson et al. |
| 2010/0169120 A1 | 7/2010 | Herbst et al. |
| 2010/0172567 A1 | 7/2010 | Prokoski |
| 2010/0176952 A1 | 7/2010 | Bajcsy et al. |
| 2010/0188228 A1 | 7/2010 | Hyland |
| 2010/0205771 A1 | 8/2010 | Pietryga et al. |
| 2010/0245577 A1 | 9/2010 | Yamamoto et al. |
| 2010/0285771 A1 | 11/2010 | Peabody |
| 2010/0305466 A1 | 12/2010 | Corn |
| 2011/0018709 A1 | 1/2011 | Kornbluh |
| 2011/0022981 A1 | 1/2011 | Mahajan et al. |
| 2011/0025493 A1 | 2/2011 | Papadopoulos et al. |
| 2011/0025499 A1 | 2/2011 | Hoy et al. |
| 2011/0035057 A1 | 2/2011 | Receveur et al. |
| 2011/0035466 A1 | 2/2011 | Panigrahi |
| 2011/0054936 A1 | 3/2011 | Cowan et al. |
| 2011/0068930 A1 | 3/2011 | Wildman et al. |
| 2011/0077965 A1 | 3/2011 | Nolte et al. |
| 2011/0087079 A1 | 4/2011 | Aarts |
| 2011/0087125 A1 | 4/2011 | Causevic |
| 2011/0102133 A1 | 5/2011 | Shaffer |
| 2011/0102181 A1 | 5/2011 | Metz et al. |
| 2011/0106560 A1 | 5/2011 | Eaton et al. |
| 2011/0106561 A1 | 5/2011 | Eaton et al. |
| 2011/0175809 A1 | 7/2011 | Markovic et al. |
| 2011/0190593 A1 | 8/2011 | McNair |
| 2011/0227740 A1 | 9/2011 | Wohltjen |
| 2011/0245707 A1 | 10/2011 | Castle et al. |
| 2011/0254682 A1 | 10/2011 | Sigrist Christensen |
| 2011/0288811 A1 | 11/2011 | Greene |
| 2011/0295621 A1 | 12/2011 | Farooq et al. |
| 2011/0301440 A1 | 12/2011 | Riley et al. |
| 2011/0313325 A1 | 12/2011 | Cuddihy |
| 2012/0016295 A1 | 1/2012 | Tsoukalis |
| 2012/0025991 A1 | 2/2012 | O'Keefe et al. |
| 2012/0026308 A1 | 2/2012 | Johnson et al. |
| 2012/0075464 A1 * | 3/2012 | Derenne ............... A61B 5/0036 600/595 |
| 2012/0092162 A1 | 4/2012 | Rosenberg |
| 2012/0098918 A1 | 4/2012 | Murphy |

(56) References Cited

U.S. PATENT DOCUMENTS

| | | |
|---|---|---|
| 2012/0140068 A1 | 6/2012 | Monroe et al. |
| 2012/0154582 A1* | 6/2012 | Johnson ............... G06Q 10/00 340/521 |
| 2012/0212582 A1 | 8/2012 | Deutsch |
| 2012/0259650 A1 | 10/2012 | Mallon et al. |
| 2012/0314901 A1 | 12/2012 | Hanson et al. |
| 2012/0323090 A1 | 12/2012 | Bechtel et al. |
| 2012/0323591 A1 | 12/2012 | Bechtel et al. |
| 2012/0323592 A1 | 12/2012 | Bechtel et al. |
| 2013/0027199 A1 | 1/2013 | Bonner |
| 2013/0028570 A1 | 1/2013 | Suematsu et al. |
| 2013/0120120 A1 | 5/2013 | Long |
| 2013/0122807 A1 | 5/2013 | Tenarvitz et al. |
| 2013/0127620 A1 | 5/2013 | Siebers et al. |
| 2013/0184592 A1* | 7/2013 | Venetianer ....... G08B 13/19615 600/476 |
| 2013/0265482 A1 | 10/2013 | Funamoto |
| 2013/0309128 A1 | 11/2013 | Voegeli et al. |
| 2013/0332184 A1 | 12/2013 | Burnham et al. |
| 2014/0039351 A1 | 2/2014 | Mix et al. |
| 2014/0070950 A1 | 3/2014 | Snodgrass |
| 2014/0081654 A1 | 3/2014 | Bechtel et al. |
| 2014/0085501 A1 | 3/2014 | Tran |
| 2014/0086450 A1 | 3/2014 | Huang et al. |
| 2014/0108041 A1 | 4/2014 | Bechtel et al. |
| 2014/0155755 A1 | 6/2014 | Pinter et al. |
| 2014/0168397 A1 | 6/2014 | Greco et al. |
| 2014/0191861 A1 | 7/2014 | Scherrer |
| 2014/0191946 A1 | 7/2014 | Cho et al. |
| 2014/0213845 A1 | 7/2014 | Bechtel et al. |
| 2014/0267625 A1 | 9/2014 | Clark et al. |
| 2014/0267736 A1 | 9/2014 | Delean |
| 2014/0309789 A1 | 10/2014 | Ricci et al. |
| 2014/0327545 A1 | 11/2014 | Bolling et al. |
| 2014/0328512 A1 | 11/2014 | Gurwicz et al. |
| 2014/0333744 A1 | 11/2014 | Baym et al. |
| 2014/0333776 A1 | 11/2014 | Dedeoglu et al. |
| 2014/0354436 A1 | 12/2014 | Nix et al. |
| 2014/0365242 A1 | 12/2014 | Neff |
| 2015/0057635 A1 | 2/2015 | Bechtel et al. |
| 2015/0061891 A1 | 3/2015 | Oleson et al. |
| 2015/0109442 A1 | 4/2015 | Derenne et al. |
| 2015/0206415 A1 | 7/2015 | Wegelin et al. |
| 2015/0269318 A1 | 9/2015 | Neff |
| 2015/0278456 A1 | 10/2015 | Bermudez Rodriguez et al. |
| 2015/0294143 A1 | 10/2015 | Wells et al. |
| 2016/0022218 A1 | 1/2016 | Hayes et al. |
| 2016/0070869 A1 | 3/2016 | Portnoy |
| 2016/0093195 A1 | 3/2016 | Ophardt |
| 2016/0127641 A1 | 5/2016 | Gove |
| 2016/0180668 A1 | 6/2016 | Kusens et al. |
| 2016/0183864 A1 | 6/2016 | Kusens et al. |
| 2016/0217347 A1 | 7/2016 | Mineo |
| 2016/0253802 A1 | 9/2016 | Venetianer et al. |
| 2016/0267327 A1 | 9/2016 | Franz et al. |
| 2016/0285416 A1 | 9/2016 | Tiwari et al. |
| 2016/0314258 A1 | 10/2016 | Kusens |
| 2016/0324460 A1 | 11/2016 | Kusens |
| 2016/0360970 A1 | 12/2016 | Tzvieli et al. |
| 2017/0055917 A1 | 3/2017 | Stone et al. |
| 2017/0084158 A1 | 3/2017 | Kusens |
| 2017/0091562 A1 | 3/2017 | Kusens |
| 2017/0109991 A1 | 4/2017 | Kusens |
| 2017/0116473 A1 | 4/2017 | Sashida et al. |
| 2017/0143240 A1 | 5/2017 | Stone et al. |
| 2017/0163949 A1 | 6/2017 | Suzuki et al. |
| 2017/0193772 A1 | 7/2017 | Kusens et al. |
| 2017/0214902 A1 | 7/2017 | Braune |
| 2017/0289503 A1 | 10/2017 | Kusens |
| 2017/0337682 A1 | 11/2017 | Liao et al. |
| 2018/0018864 A1 | 1/2018 | Baker |
| 2018/0068545 A1 | 3/2018 | Kusens |
| 2018/0104409 A1 | 4/2018 | Bechtel et al. |
| 2018/0114053 A1 | 4/2018 | Kusens et al. |
| 2018/0116528 A1 | 5/2018 | Tzvieli et al. |
| 2018/0144605 A1 | 5/2018 | Kusens |
| 2018/0189946 A1 | 7/2018 | Kusens et al. |
| 2018/0190098 A1 | 7/2018 | Kusens |
| 2018/0357875 A1 | 12/2018 | Kusens |
| 2019/0006046 A1 | 1/2019 | Kusens et al. |
| 2019/0029528 A1 | 1/2019 | Tzvieli et al. |
| 2019/0043192 A1 | 2/2019 | Kusens et al. |
| 2019/0057592 A1 | 2/2019 | Kusens |
| 2019/0122028 A1 | 4/2019 | Kusens et al. |
| 2019/0205630 A1 | 7/2019 | Kusens |
| 2019/0206218 A1 | 7/2019 | Kusens et al. |
| 2019/0209022 A1 | 7/2019 | Sobol et al. |
| 2019/0228866 A1 | 7/2019 | Weffers-Albu et al. |
| 2019/0253668 A1 | 8/2019 | Kusens |
| 2019/0307405 A1 | 10/2019 | Terry et al. |
| 2019/0318149 A1 | 10/2019 | Kusens et al. |
| 2020/0050844 A1 | 2/2020 | Kusens |
| 2020/0226905 A1 | 7/2020 | Kusens et al. |
| 2021/0202052 A1 | 7/2021 | Bechtel et al. |

FOREIGN PATENT DOCUMENTS

| | | |
|---|---|---|
| WO | 2009/018422 A1 | 2/2009 |
| WO | 2012/122002 A1 | 9/2012 |

OTHER PUBLICATIONS

Final Office Action received for U.S. Appl. No. 15/134,189, dated May 6, 2020, 31 pages.

Preinterview First Office Action received for U.S. Appl. No. 16/181,897 dated May 11, 2020, 5 pages.

Non-Final Office action received for U.S. Appl. No. 16/410,745, dated May 21, 2021, 21 pages.

Conaire et al., "Fusion of Infrared and Visible Spectrum Video for Indoor Surveillance", WIAMIS, Apr. 2005, 4 pages.

Mooney, Tom, "Rhode Island ER First to Test Google Glass on Medical Conditions", EMS1, Available online at: <https://www.ems1.com/ems-products/technology/articles/1860487-Rhode-Island-ER-first-to-test-Google-Glass-on-medical-conditions/>, Mar. 10, 2014, 3 pages.

Raheja et al., "Human Facial Expression Detection From Detected in Captured Image Using Back Propagation Neural Network", International Journal of Computer Science and Information Technology (IJCSIT), vol. 2, No. 1, Feb. 2010, 9 pages.

"Virtual Patient Observation: Centralize Monitoring of High-Risk Patients with Video", Cisco, Cisco Video Surveillance Manager, 2013, pp. 1-6.

Notice of Allowance received for U.S. Appl. No. 16/181,897, dated Oct. 14, 2020, 9 pages.

Preinterview First Office Action received for U.S. Appl. No. 16/832,790, dated Aug. 25, 2020, 5 pages.

Non-Final Office Action received for U.S. Appl. No. 17/101,639, dated Sep. 13, 2021, 2021, 13 pages.

Notice of Allowance received for U.S. Appl. No. 16/816,626, dated Sep. 30, 2021, 9 pages.

Quan et al., "Facial Asymmetry Analysis Based on 3-D Dynamic Scans", 2012 IEEE International Conference on Systems, Man, and Cybernetics; COEX, Seoul, Korea; DOI: 10.1109/ICSMC.2012.6378151, Oct. 14-17, 2012, pp. 2676-2681.

Non-Final Office action received for U.S. Appl. No. 17/117,414, dated Jul. 27, 2021, 12 pages.

Pre-interview First Office Action received for U.S. Appl. No. 16/731,274, dated Sep. 1, 2021, 12 pages.

Notice of Allowance received for U.S. Appl. No. 16/654,502, dated Feb. 17, 2021, 9 pages.

Notice of Allowance received for U.S. Appl. No. 16/410,745, dated Jan. 4, 2022, 10 pages.

\* cited by examiner

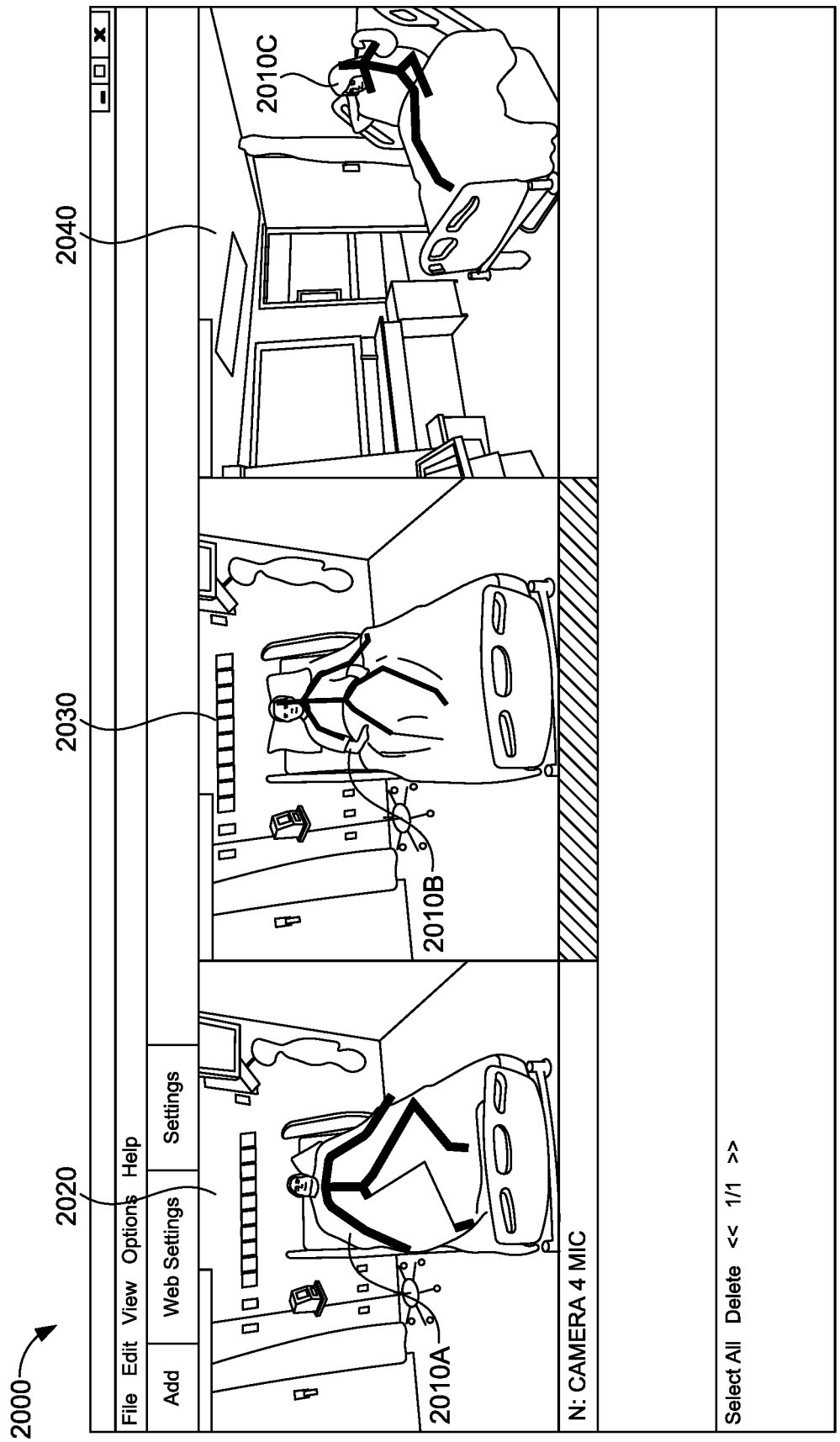

DETECTING UNAUTHORIZED VISITORS

CROSS-REFERENCE TO RELATED APPLICATIONS

This application is a continuation of and claims priority to co-pending U.S. patent application Ser. No. 16/454,508, filed Jun. 27, 2019, which is a continuation of and claims priority to U.S. Pat. No. 10,410,042, issued Sep. 10, 2019, which is a continuation of and claims priority to U.S. Pat. No. 10,210,378 issued Feb. 19, 2019, which is a continuation of and claims priority to U.S. Pat. No. 9,892,311 issued Feb. 13, 2018, which claims priority to U.S. Provisional Application Ser. No. 62/273,735 filed Dec. 31, 2015, each of which are herein incorporated by reference in their entireties.

BACKGROUND

Medical facilities, such as hospitals, face many challenges in addition to simply caring for patients. For example, securing patients and equipment (e.g., medical devices) consumes many resources and current methods lack effectiveness. In addition to requiring personnel to physically monitor locations within the facility, visitor logs, visitor badges, and radio-frequency identification (RFID) technology are often utilized to control access to certain locations within the facility. However, each of these require subjective decision-making and are prone to error by the personnel monitoring the locations or assisting visitors signing a visitor log and issuing visitor badges accordingly. Further, none of these methods necessarily prevent an authorized visitor from breaching areas of the facility where the authorized visitor is not authorized. For example, a visitor may be authorized to visit a particular patient but, based on some condition of the patient, may not have close contact with the patient. In contrast, a caregiver of the same patient may need to have close contact with the patient. Additionally, in some situations, an authorized visitor may unwittingly provide contraband (e.g., some thing or some object a particular patient is not allowed) to a patient that the current methods are unable to detect. Finally, medical devices are constantly being shuffled between patients and locations within a facility. Tracking the locations of these devices can be extremely difficult. Accordingly, overall security for patients and equipment suffers, and the many resources currently being utilized are wasted.

BRIEF SUMMARY

This brief summary is provided as a general overview of the more detailed disclosure which follows. It is not intended to identify key or essential elements of the disclosure, or to define the claim terms in isolation from the remainder of the disclosure, including the drawings.

This disclosure generally relates to methods and systems for detecting unauthorized visitors in medical facilities. Generally, and without limitation, the method involves collecting an image of a person detected in a room of a patient. The system identifies reference points on the person's face, for example, points along the cheeks, jowls, and/or brow. The system may compare the reference points to reference points of images associated with registered visitors. The system then determines, based on the comparison, if the person is a registered visitor. One or more designated recipients may be alerted if the person is not a registered visitor or if the person breaches a patient identification zone established around a particular patient. The system may also register the person in a database of visitors.

In some aspects, this disclosure relates to a method for detecting unauthorized visitors. The method comprises: receiving from a 3D motion sensor an image of a person detected in a room of a patient; comparing positions of a plurality of reference points of the image to positions of a plurality of registered reference points of images associated with registered visitors, the plurality of registered reference points of images associated with registered visitors stored in a database of registered visitors; determining, based on the comparing, if the person is a registered visitor; and registering the person, if the determining indicates the person is not a registered visitor.

In some aspects, this disclosure relates to a system for detecting unauthorized visitors. The system comprises: one or more 3D motion sensors located to provide the one or more 3D motion sensors with a view of a person to be monitored, the 3D motion sensors configured to collect a series of images of the face of the person; a computerized monitoring system communicatively coupled to the one or more 3D motion sensors, the computerized monitoring system configured to identify a plurality of reference points on the face of the person and to compare positions of the plurality of the reference points to positions of a plurality of registered reference points on the face of registered visitors to determine if the person is a registered visitor, the plurality of registered reference points on the face of registered visitors stored in a database; and a computerized communication system communicatively coupled to the computerized monitoring system, the computerized communication system configured to send an alert to one or more designated recipients if the person is not a registered visitor and is determined to be an unauthorized visitor for the patient.

The unauthorized visitor system may further comprise a central video monitoring system. The central video monitoring system may be communicatively coupled to the computerized communication system. The central video monitoring system may be configured to display an image of the person. The central video monitoring system may comprise a primary display. The central video monitoring system may comprise an alert display. The alert display may be a dedicated portion of the primary display. The alert display may be a separate display or series of displays from the primary display. If the computerized patient monitoring system detects a person that is not a registered visitor, the central communication system may be configured to send an alert to the central video monitoring system. The central video monitoring system may be configured to move the display of the image of the person from the primary display to the alert display upon receipt of an alert.

In some aspects, this disclosure relates to computer-readable storage media having embodied thereon computer-executable instructions. When executed by one or more computer processors, the instructions may cause the processors to: receive from a 3D motion sensor an image of a person detected in a room of a patient; compare the image of the person to images of registered visitors stored in a database of registered visitors; determine, based on the comparing, if the person is a registered visitor; and alert one or more designated recipients if the person is not a registered visitor and is determined to be an unauthorized visitor for the patient.

Additional objects, advantages, and novel features of the disclosure will be set forth in part in the description which follows, and in part will become apparent to those skilled in the art upon examination of the following, or may be learned by practice of the disclosure.

BRIEF DESCRIPTION OF THE SEVERAL VIEWS OF THE DRAWINGS

The description references the attached drawing figures, wherein:

FIGS. 7-20 are exemplary displays for unauthorized visitor detection systems, in accordance with embodiments of the present disclosure.

DETAILED DESCRIPTION

As noted in the Background, medical facilities, such as hospitals, face many challenges in addition to simply caring for patients. For example, securing patients and equipment (e.g., medical devices) consumes many resources and current methods lack effectiveness. In addition to requiring personnel to physically monitor locations within the facility, visitor logs, visitor badges, and radio-frequency identification (RFID) technology are often utilized to control access to certain locations within the facility. However, each of these require subjective decision-making and are prone to error by the personnel monitoring the locations or assisting visitors signing a visitor log and issuing visitor badges accordingly. Further, none of these methods necessarily prevent an authorized visitor from breaching areas of the facility where the authorized visitor is not authorized. For example, a visitor may be authorized to visit a particular patient but is not authorized to visit another patient or particular areas of the facility. Additionally, in some situations, an authorized visitor may unwittingly provide contraband (e.g., some thing or some object a particular patient is not allowed to possess or be near) to a patient that the current methods are unable to detect. Finally, medical devices are constantly being shuffled between patients and locations within a facility. Tracking the locations of these devices can be extremely difficult. Accordingly, overall security for patients and equipment suffers, and the many resources currently being utilized are wasted.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Figure 1:
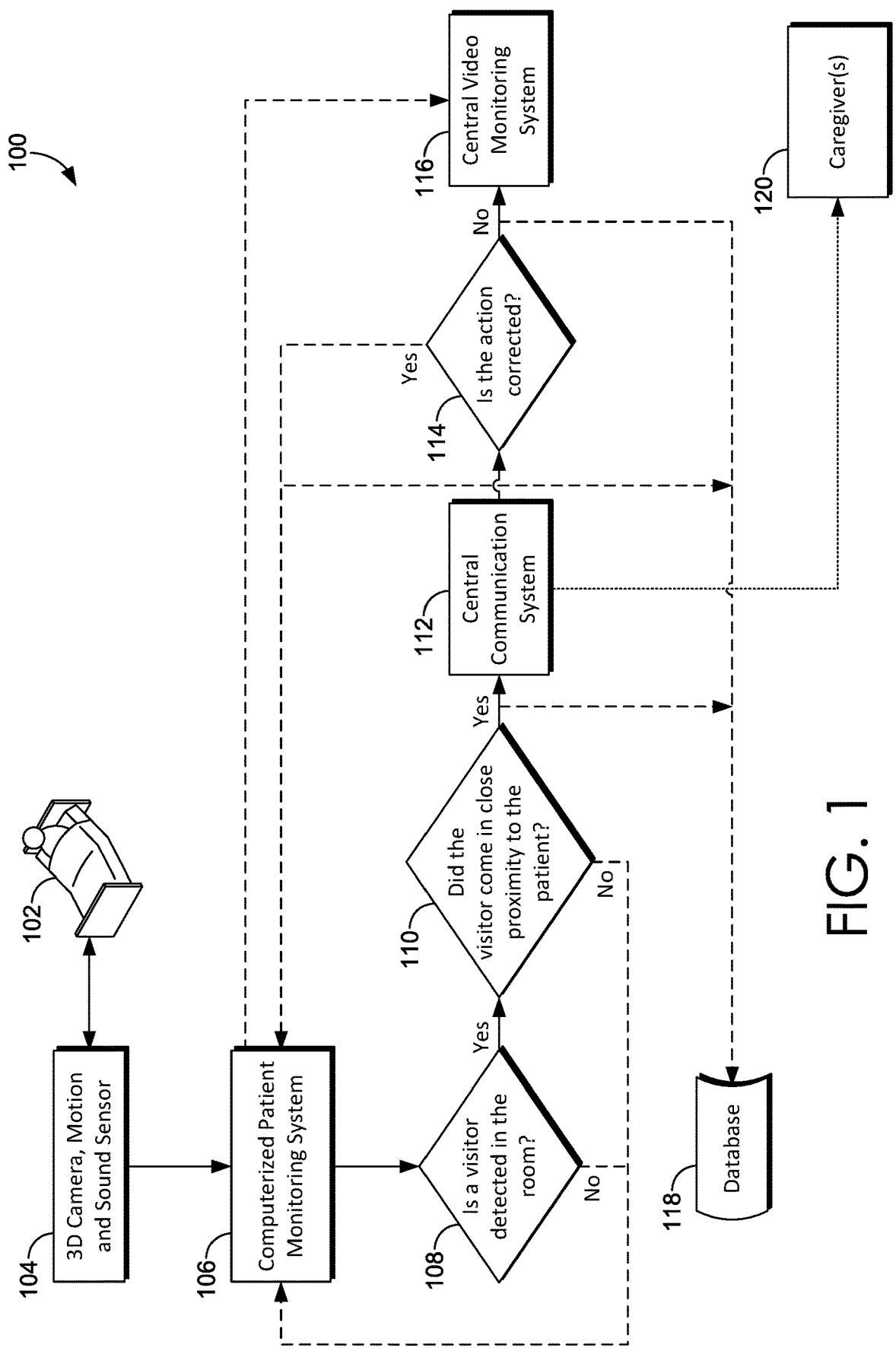
FIGS. 1-6 are exemplary flowcharts for unauthorized visitor detection systems, in accordance with embodiments of the present disclosure.

As shown in FIG. 1, a system for detecting unauthorized visitors 100 may include one or more 3D motion sensors 104. A 3D motion sensor is an electronic device that contains one or more cameras capable of identifying individual objects, people, and motion. The 3D motion sensor may further contain one or more microphones to detect audio. The cameras can utilize technologies including but not limited to color RGB, CMOS sensors, lasers, infrared projectors, and RF-modulated light. The 3D motion sensor may have one or more integrated microprocessors and/or image sensors to detect and process information both transmitted from and received by the various cameras. Exemplary 3D motion sensors include the Microsoft® Kinect® Camera, the Sony® PlayStation® Camera, and the Intel® RealSense™ Camera, each of which happens to include microphones, although sound capture is not essential to the practice of the disclosure. A user may be able to configure alerts based on data that is received from the 3D motion sensor 104 and interpreted by the computerized patient monitoring system 106. For example, a user can configure the computerized patient monitoring system 106 to provide alerts based on data the computerized patient monitoring system 106 has interpreted for setting zones in a patient's room, comparing data from multiple systems (RTLS or facial recognition) to determine authorized visitors, a patient crossing a trip wire, falling on the ground, or entering or exiting a safety zone.

As used herein, "a sensor" and "sensors" are used interchangeably in the singular and plural unless expressly described as a singular sensor or an array of sensors. A singular sensor may be used, or a sensor may comprise two or more cameras integrated into a single physical unit. Alternately, two or more physically distinct sensors may be used, or two or more physically distinct arrays of sensors may be used.

An "unauthorized visitor" may be a person in the room of a patient being monitored that is already registered in a database of persons (e.g., caregiver, staff, or visitor), but not allowed to be in close proximity to the patient. An unauthorized visitor may be a person in the room of the patient being monitored that has not yet been registered in a database of persons.

A 3D motion sensor 104 may be co-located with a patient 102 to be monitored. The patient 102 to be monitored may be monitored in a variety of environments, including, without limitation, a hospital, a home, a hospice care facility, a nursing home, an assisted living facility, an outpatient medical care facility, and the like. The 3D motion sensor 104 may be positioned where it is likely to capture skeletal tracking of the patient 102 to be monitored or visitors entering the room. For example, a 3D motion sensor 104 may be oriented to take images of a bed, chair, or other location where the patient 102 to be monitored or visitors entering the room may spend a significant amount of time. The 3D motion sensor 104 may be permanently installed, or may be temporarily set up in a room as needed. The patient 102 to be monitored may be under immediate medical care (e.g., in a medical facility under the supervision of a medical professional) or may not be under immediate care (e.g., in a home or other environment, possibly with a caregiver). A caregiver may be a medical professional or paraprofessional, such as an orderly, nurse's aide, nurse, or the like. A caregiver may also be a friend, relative, individual, company, or facility that provides assistance with daily living activities and/or medical care for individuals, such as individuals who are disabled, ill, injured, elderly, or otherwise in need of temporary or long-term assistance. In some instances, the person to be monitored may be self-sufficient and not under the immediate care of any other person or service provider.

The 3D motion sensor 104 may communicate data, such as skeletal images of the patient 102 being monitored or a visitor detected in the room, to a computerized patient monitoring system 106. The computerized patient monitoring system 106 is a computer programmed to monitor transmissions of data from the 3D motion sensor 104. The computerized patient monitoring system 106 may be integral to the 3D motion sensor 104 or a distinctly separate apparatus from the 3D motion sensor 104, possibly in a remote location from 3D motion sensor 104 provided that the computerized patient monitoring system 106 can receive data from the 3D motion sensor 104. The computerized patient monitoring system 106 may be located in the monitored person's room, such as a hospital room, bedroom, or living room. The computerized patient monitoring system 106 may be connected to a central video monitoring system 116. The computerized patient monitoring system 106 and central video monitoring system 116 may be remotely located at any physical locations so long as a data connection exists (USB, TCP/IP, or comparable) between the computerized patient monitoring system 106, the central communication system 112 (if separate from computerized patient monitoring system 106), the central video monitoring system 116, and the 3D motion sensor(s) 104.

The computerized patient monitoring system 106 may receive data from 3D motion sensor 104 for a monitoring zone (i.e., the patient's room or area to be monitored). At step 108, the computerized patient monitoring system 106 may assess whether a visitor is detected in the room using skeletal tracking based on detecting a skeleton in addition to the skeleton of the patient. If a visitor is not detected in the room, the computerized patient monitoring system 106 may continue to analyze images in the monitoring zone as long as 3D motion sensor 104 continues to transmit data.

If a visitor is detected within the monitoring zone at step 108 (via skeletal tracking indicating that two skeletons are too close to each other), computerized patient monitoring system 106 may, at step 110, determine whether the visitor was in proximity to the patient. Computerized patient monitoring system 106 may establish a patient identification zone within the monitoring zone that, if crossed by a visitor, establishes that the visitor was in proximity to the patient. Such a patient identification zone may also be configured by an administrator of the computerized patient monitoring system 106. Patient identification zones can be established using any shapes, including, without limitation, rectangles, squares, circles, ovals, triangles, and irregular shapes.

Computerized patient monitoring system 106 may assign reference points to identify the boundaries of the patient identification zone. For example, reference points may be assigned to a perimeter around the patient. It should be understood that the selection of the reference points may vary with the individual and/or the configuration of the monitoring system 100. Reference points may be configured automatically by the monitoring system 100, may be configured automatically by the monitoring system 100 subject to confirmation and/or modification by a system user, or may be configured manually by a system user.

On detecting the visitor came into close proximity to the patient, such as by entering the patient identification zone, and is now considered an unauthorized visitor, central communication system 112 may be configured to send an alert of the unauthorized visitor to one or more designated recipients (e.g., caregiver(s) 120). Central communication system 112 may be an integral part of computerized patient monitoring system 106 and/or may be implemented using separate software, firmware and/or hardware, possibly physically remote from central communication system 112.

When an alert is triggered, the alert may be sent, at least initially, to the patient 102 being monitored, to give the patient 102 being monitored an opportunity to respond before alerting the central video monitoring system 116 and/or caregiver(s) 120. For example, an audible message may be played in the room where patient 102 is being monitored, possibly asking something such as, "Please refrain from close contact with the patient."

Shown as step 114 in FIG. 1, computerized patient monitoring system 106 can analyze subsequent image data from 3D motion sensor 104 for corrective action such as the unauthorized visitor moving out of the patient identification zone or gestures, such as a head nod, consistent with a yes or no answer to determine if the action will be corrected. If 3D motion sensor 104 is equipped with microphones, computerized patient monitoring system 106 can analyze sound data for recognizable words, such as okay, yes, or no, help.

Central video monitoring system 116 may be alerted if no response is received at step 114, or if the response is unintelligible or indicates that the patient 102 being monitored and/or the unauthorized visitor does not intend to comply with the patient identification zone requirements. Alternately, or additionally, central video monitoring system 116 may be alerted with or even before patient 102, so that central video monitoring system 116 can determine whether the unauthorized visitor detected is, in fact, problematic. On receiving an alert, the central video monitoring system 116, or an attendant there, may view live image, video, and/or audio feed from the 3D motion sensor 104 and evaluate whether the unauthorized visitor presents a danger to the patient and/or himself. If patient 102 has been alerted by the central communication system 112, central video monitoring system 116 or an attendant there can use the data from 3D motion sensor 104 to evaluate whether a response from patient 102 indicates that patient 102 or the unauthorized visitor is complying with the patient identification zone requirements. Central video monitoring system 116 and/or computerized patient monitoring system 106 may analyze the response from patient 102 and/or the unauthorized visitor, however, if the response does not include words or gestures recognizable by the computerized system, an attendant at central video monitoring system 116 may be able to interpret the person's response. If needed, the central video monitoring system 116 and/or the attendant could then approve alert(s) to appropriate caregiver(s) 120 and/or call for emergency assistance (e.g., send a request for security).

One or more caregiver(s) 120 local to patient 102 can be alerted with or even before patient 102 and/or central video monitoring system 116, so that the caregiver(s) 120 can assess what is happening in person. Or, monitored patient 102, caregiver(s) 120, and the central video monitoring system 116 could all be alerted at the same time. The priority and timing of alerts to different individuals or stations can be configured in accordance with the needs and desires of a particular facility, experience with a particular monitored individual or type of patient, or any other criterion of the system owner or user. This is true for initial alerts as well as continuing alerts (e.g., if an unauthorized visitor is detected in and remains in close proximity to the patient 102, and no response from patient 102 or a caregiver 120 is received or observed) or repeated alerts (two or more distinct events where an unauthorized visitor is detected in close proximity to the patient 102). The priority and timing of alerts to different individuals may be different for initial, continuing, and/or repeated alerts.

Data associated with alerts may be logged by computerized patient monitoring system 106 and/or central video monitoring system 116 in a database 118. Data associated with an alert may include, without limitation, the telemetry data from 3D motion sensor 104 that triggered the alert; buffered data preceding the telemetry data that triggered the alert; telemetry data subsequent to the alert; the number and substantive content of an alert; the individual(s) and/or groups to whom an alert was addressed; the response, if any, received or observed following an alert; and combinations thereof.

Figure 2:
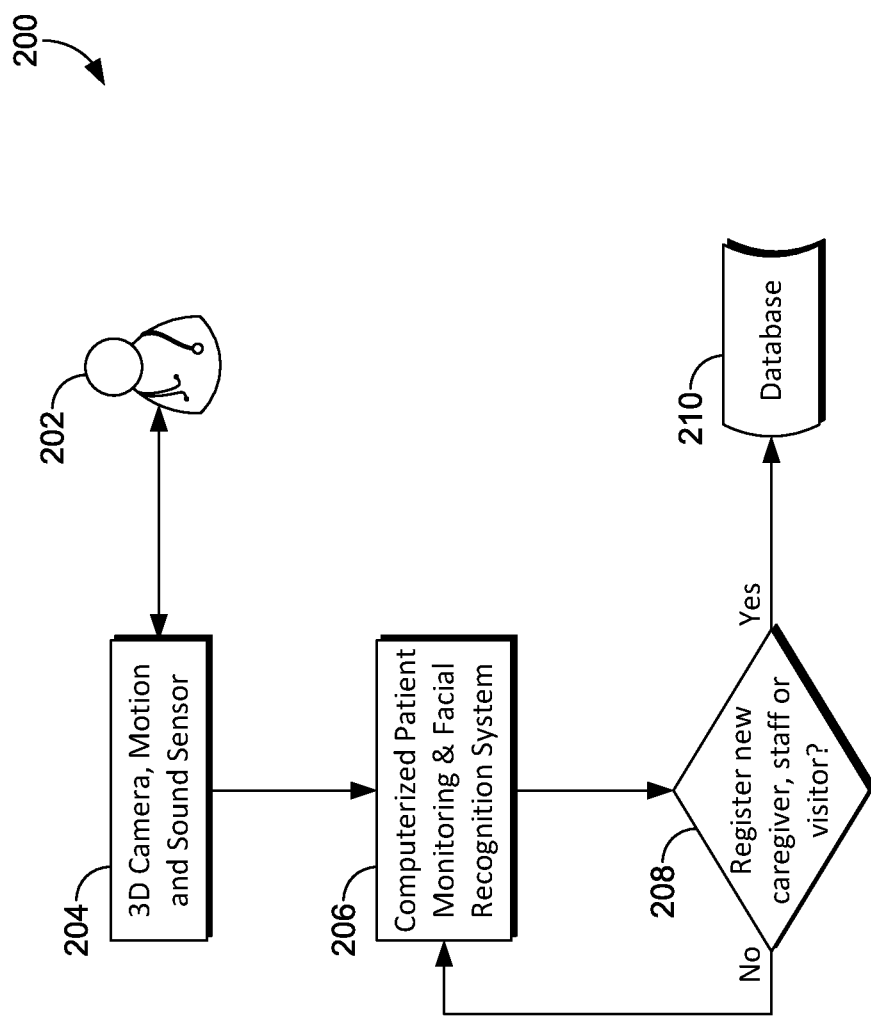

As shown in FIG. 2, unauthorized visitor system 200 may be utilized to register a person(s) 202 entering the room of a patient. For example, 3D motion sensor 204 may detect a person 202 entering the room of the patient. Facial features of the visitor may be analyzed by computerized patient monitoring and facial recognition system 206 to determine if the visitor has a recognition profile stored in database 210. If the person is registered (i.e., indicating a recognition profile of the person has been stored in database 210), no further action is taken. If the person is not registered in database 210, a recognition profile is created for the person in database 210. The recognition profile may include an image of the person, identifying information indicating whether the person is a caregiver, staff, or visitor, and any rights and/or privileges that person may have.

Figure 3:
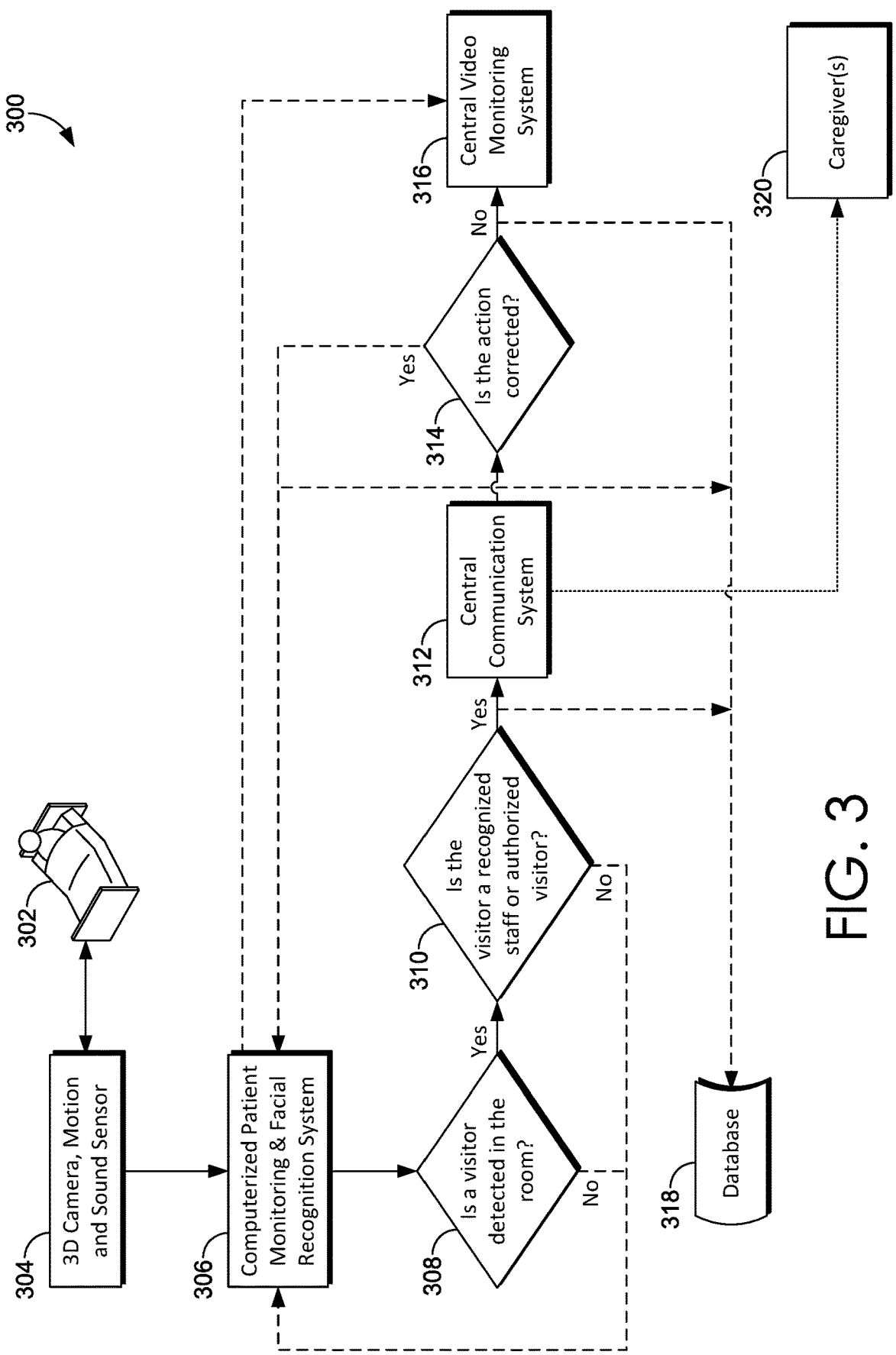

In FIG. 3, a 3D motion sensor 304 may be co-located with a patient 302 to be monitored. The patient 302 to be monitored may be monitored in a variety of environments, including, without limitation, a hospital, a home, a hospice care facility, a nursing home, an assisted living facility, an outpatient medical care facility, and the like. The 3D motion sensor 304 may be positioned where it is likely to capture images of the face of the patient 302 to be monitored. For example, a 3D motion sensor 304 may be oriented to take images of a bed, chair, or other location where the patient 302 to be monitored may spend a significant amount of time. In some embodiments, the 3D motion sensor 304 may be oriented to take images of persons entering and exiting the room of the patient 302 to be monitored. In some embodiments, the 3D motion sensor 304 may be oriented to take images of items or equipment (e.g., medical devices) that may be located in the room of the patient 302 to be monitored. The 3D motion sensor 304 may be permanently installed or may be temporarily set up in a room as needed. The patient 302 to be monitored may be under immediate medical care, e.g., in a medical facility under the supervision of a medical professional, or may not be under immediate care, e.g., in a home or other environment, possibly with a caregiver. A caregiver may be a medical professional or paraprofessional, such as an orderly, nurse's aide, nurse, or the like. A caregiver may also be a friend, relative, individual, company, or facility that provides assistance with daily living activities and/or medical care for individuals, such as individuals who are disabled, ill, injured, elderly, or otherwise in need of temporary or long-term assistance. In some instances, the person to be monitored may be self-sufficient and not under the immediate care of any other person or service provider.

The 3D motion sensor 304 may communicate data, such as images of the patient 302 being monitored or a visitor detected in the room, to a computerized patient monitoring system 306. The computerized patient monitoring system 306 is a computer programmed to monitor transmissions of data from the 3D motion sensor 304. The computerized patient monitoring system 306 may be integral to the 3D motion sensor 304 or a distinctly separate apparatus from the 3D motion sensor 304, possibly in a remote location from 3D motion sensor 304 provided that the computerized patient monitoring system 306 can receive data from the 3D motion sensor 304. The computerized patient monitoring system 306 may be located in the monitored person's room, such as a hospital room, bedroom, or living room. The computerized patient monitoring system 306 may be connected to a central video monitoring system 316. The computerized patient monitoring system 306 and central video monitoring system 316 may be remotely located at any physical locations so long as a data connection exists (USB, TCP/IP, or comparable) between the computerized patient monitoring system 306, the central communication system 312 (if separate from the computerized patient monitoring system 306), the central video monitoring system 316, and the 3D motion sensor(s) 304.

The computerized patient monitoring system 306 may receive data from 3D motion sensor 304 for a monitoring zone (i.e., the patient's room or area to be monitored). At step 308, the computerized patient monitoring system 306 may assess whether a visitor is detected in the room. If a visitor is not detected in the room, the computerized patient monitoring system 306 may continue to analyze images in the monitoring zone as long as 3D motion sensor 304 continues to transmit data.

If a visitor is detected (via skeletal tracking or blob recognition) within the monitoring zone at step 308, computerized patient monitoring system 306 may, at step 310, determine whether the visitor is an authorized visitor (via facial recognition). To do so, computerized patient monitoring system 306 may assign reference points to distinctive features of the image of the visitor. For example, reference points may be assigned around the eyes and around the mouth of the visitor. It should be understood that the selection of the reference points may vary with the individual and/or the configuration of the monitoring system 300. For example, if bandages or physiological anomalies would complicate the tracking of routine reference points, alternative reference points may be assigned. Reference points may be configured automatically by the monitoring system 300, may be configured automatically by the monitoring system 300 subject to confirmation and/or modification by a system user, or may be configured manually by a system user. The reference points corresponding to the visitor may be compared to a database comprising reference points of known or authorized visitors. Various machine learning and/or facial recognition techniques may additionally be utilized to determine if the visitor is an authorized visitor. If no match is found in the database of known visitors, the visitor may be an unauthorized visitor.

Accordingly, computerized patient monitoring system 306 may communicate an image of the visitor to central communication system 312. Central communication system 312 may be configured to send an alert of the unauthorized visitor to one or more designated recipients (e.g., caregiver(s) 320). Central communication system 312 may be an integral part of computerized patient monitoring system 306 and/or may be implemented using separate software, firmware, and/or hardware, possibly physically remote from central communication system 312. When an alert is triggered, the alert may be sent, at least initially, to the patient 302 being monitored to give the patient 302 being monitored an opportunity to respond before alerting the central video monitoring system 316 and/or caregiver(s) 320. For example, an audible message may be played in the room where patient 302 is being monitored, possibly asking the visitor: "Please show your identification."

Shown as step 314 in FIG. 3, computerized patient monitoring system 306 can analyze subsequent image data from 3D motion sensor 304 for corrective action such as the unauthorized visitor adequately providing identification, such as by showing identifying or providing an indication consistent with a yes or no answer to determine if the action will be corrected. If 3D motion sensor 304 is equipped with microphones, computerized patient monitoring system 306 can analyze sound data for recognizable words, such as okay, yes, or no, help.

Central video monitoring system 316 may be alerted if no response is received at step 314 or if the response is unintelligible or indicates that the unauthorized visitor does not intend to comply. Alternately, or additionally, central video monitoring system 316 may be alerted with or even before patient 302, so that central video monitoring system 316 can determine whether the unauthorized visitor detected is, in fact, problematic. On receiving an alert, the central video monitoring system 316, or an attendant there, may view live image, video, and/or audio feed from the 3D motion sensor 304 and evaluate whether the unauthorized visitor presents a danger to the patient and/or himself. If patient 302 has been alerted by the central communication system 312, central video monitoring system 316 or an attendant there can use the data from 3D motion sensor 304 to evaluate whether a response from patient 302 indicates that the unauthorized visitor is complying with identification requirements. Central video monitoring system 316 and/or computerized patient monitoring system 306 may analyze the response from patient 302 and/or the unauthorized visitor, however, if the response does not include words or gestures recognizable by the computerized system, an attendant at central video monitoring system 316 may be able to interpret the person's response. If needed, the central video monitoring system 316 and/or the attendant could then approve alert(s) to appropriate caregiver(s) 320 and/or call for emergency assistance (e.g., send a request for security).

One or more caregiver(s) 320 local to patient 302 can be alerted with or even before patient 302 and/or central video monitoring system 316, so that the caregiver(s) 320 can assess what is happening in person. Or, monitored patient 302, caregiver(s) 320 and the central video monitoring system 316 could all be alerted at the same time. The priority and timing of alerts to different individuals or stations can be configured in accordance with the needs and desires of a particular facility, experience with a particular monitored individual or type of patient, or any other criterion of the system owner or user. This is true for initial alerts as well as continuing alerts (e.g., if an unauthorized visitor is detected, and no response is received or observed) or repeated alerts (two or more distinct events where an unauthorized visitor is detected). The priority and timing of alerts to different individuals may be different for initial, continuing, and/or repeated alerts.

Data associated with alerts may be logged by computerized patient monitoring system 306 and/or central video monitoring system 316 in a database 318. Data associated with an alert may include, without limitation, the telemetry data from 3D motion sensor 304 that triggered the alert; buffered data preceding the telemetry data that triggered the alert; telemetry data subsequent to the alert; the number and substantive content of an alert; the individual(s) and/or groups to whom an alert was addressed; the response, if any, received or observed following an alert; and combinations thereof. In embodiments, data for authorized visitors (e.g., recognition profile) may also be stored in database 318.

Figure 4:
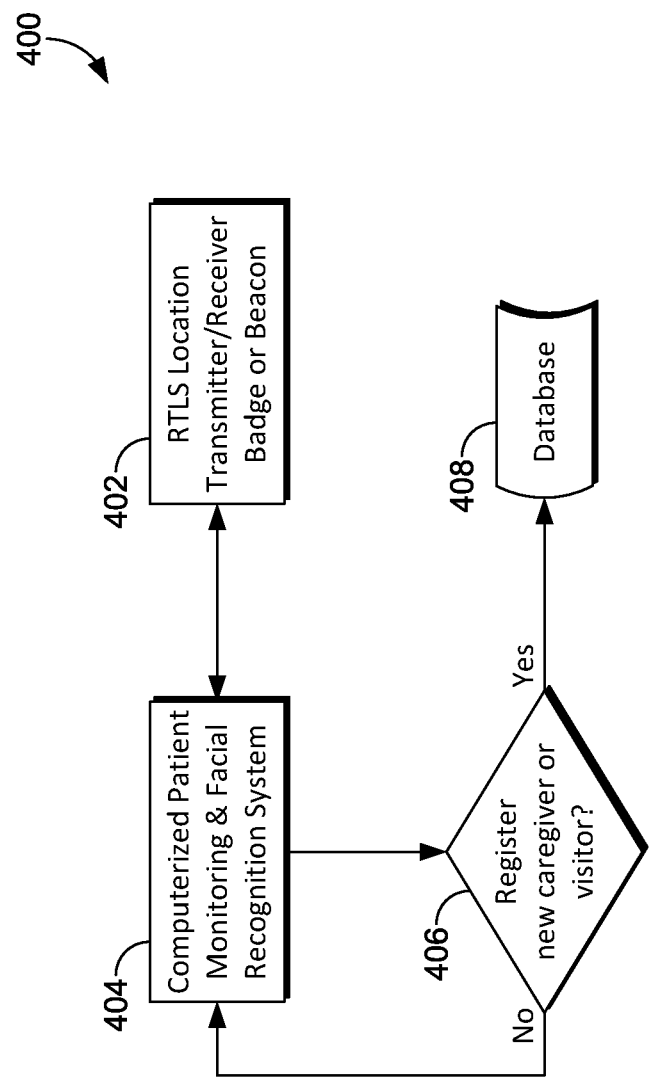

As shown in FIG. 4, unauthorized visitor system 400 may be utilized in connection with a real-time locating system (RTLS) to register a person(s) entering the room of a patient. For example, RTLS may detect a signal from an electronic transmitter (e.g., RFID, Bluetooth Low Energy, Wi-Fi, ultrasound, infrared, Light Fidelity, and the like) worn by the person detected, as shown at 402, indicating a person has entered the room of the patient. Computerized patient monitoring and facial recognition system, as shown at step 404, receives the signal from the badge. If the person is a new caregiver or visitor, as shown at step 406, the person is registered in database 408. If the person is not a new caregiver or visitor, as shown at step 406, the person is not registered in the database 408.

Figure 5:
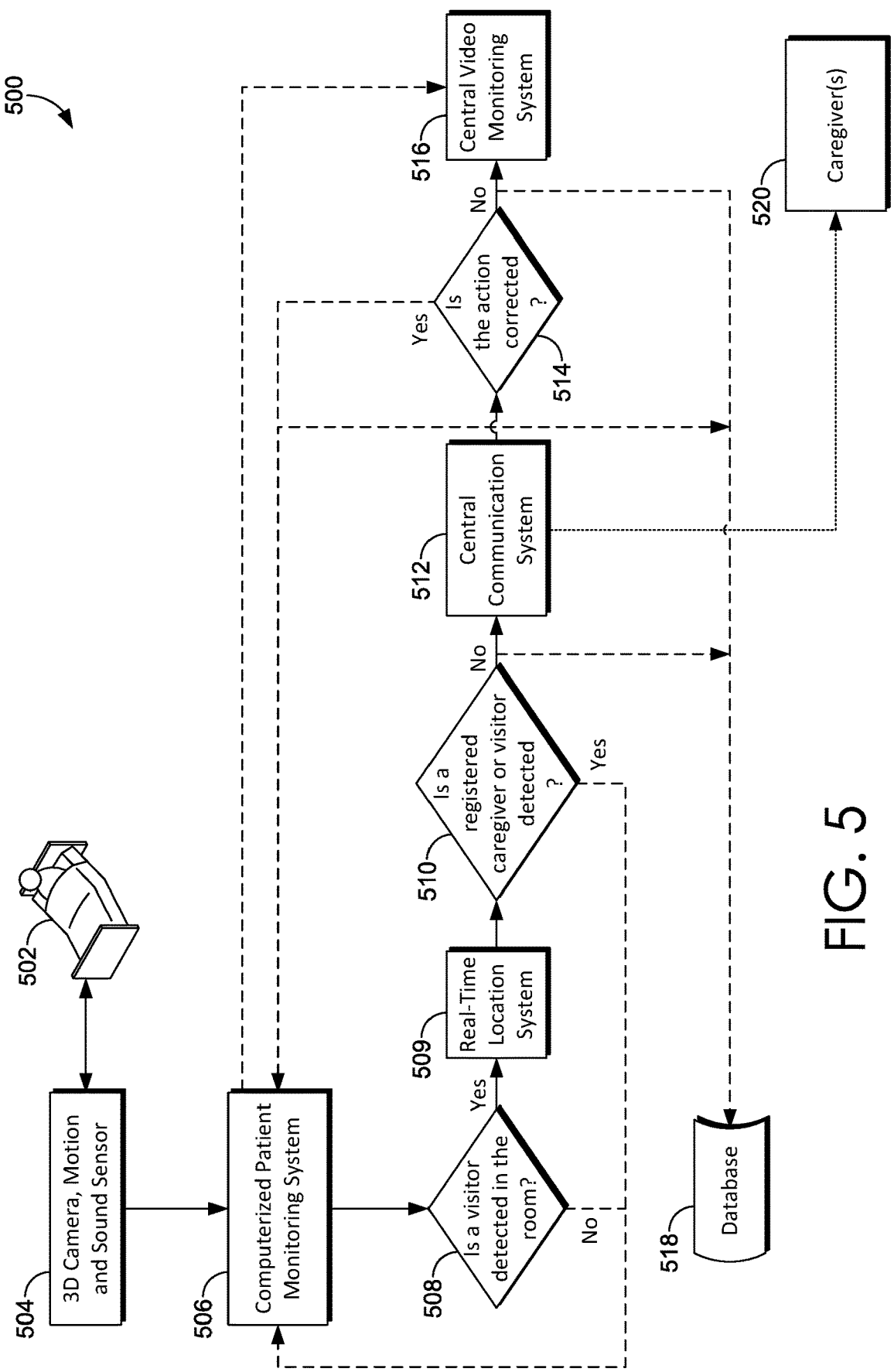

In FIG. 5, a 3D motion sensor 504 may be co-located with a patient 502 to be monitored. The patient 502 to be monitored may be monitored in a variety of environments, including, without limitation, a hospital, a home, a hospice care facility, a nursing home, an assisted living facility, an outpatient medical care facility, and the like. The 3D motion sensor 504 may be positioned where it is likely to capture images of the face of the patient 502 to be monitored. For example, a 3D motion sensor 504 may be oriented to take images of a bed, chair, or other location where the patient 502 to be monitored may spend a significant amount of time. In some embodiments, the 3D motion sensor 504 may be oriented to take images of persons entering and exiting the room of the patient 502 to be monitored. In some embodiments, the 3D motion sensor 504 may be oriented to take images of items or equipment (e.g., medical devices) that may be located in the room of the patient 502 to be monitored. The 3D motion sensor 504 may be permanently installed or may be temporarily set up in a room as needed. The patient 502 to be monitored may be under immediate medical care, e.g., in a medical facility under the supervision of a medical professional, or may not be under immediate care, e.g., in a home or other environment, possibly with a caregiver. A caregiver may be a medical professional or paraprofessional, such as an orderly, nurse's aide, nurse, or the like. A caregiver may also be a friend, relative, individual, company, or facility that provides assistance with daily living activities and/or medical care for individuals, such as individuals who are disabled, ill, injured, elderly, or otherwise in need of temporary or long-term assistance. In some instances, the person to be monitored may be self-sufficient and not under the immediate care of any other person or service provider.

The 3D motion sensor 504 may communicate data, such as images of the patient 502 being monitored or a visitor detected in the room, to a computerized patient monitoring system 506. The computerized patient monitoring system 506 is a computer programmed to monitor transmissions of data from the 3D motion sensor 504. The computerized patient monitoring system 506 may be integral to the 3D motion sensor 504 or a distinctly separate apparatus from the 3D motion sensor 504, possibly in a remote location from 3D motion sensor 504 provided that the computerized patient monitoring system 506 can receive data from the 3D motion sensor 504. The computerized patient monitoring system 506 may be located in the monitored person's room, such as a hospital room, bedroom, or living room. The computerized patient monitoring system 506 may be connected to a central video monitoring system 516. The computerized patient monitoring system 506 and central video monitoring system 516 may be remotely located at any physical locations so long as a data connection exists (USB, TCP/IP, or comparable) between the computerized patient monitoring system 506, the central communication system 512 (if separate from computerized patient monitoring system 506), the central video monitoring system 516, and the 3D motion sensor(s) 504.

The computerized patient monitoring system 506 may receive data from 3D motion sensor 504 for a monitoring zone (i.e., the patient's room or area to be monitored). At step 508, the computerized patient monitoring system 506 may assess whether a visitor is detected in the room (via skeletal tracking or blob recognition). If a visitor is not detected in the room, the computerized patient monitoring system 506 may continue to analyze images in the monitoring zone as long as 3D motion sensor 504 continues to transmit data.

If a visitor is detected within the monitoring zone at step 508, computerized patient monitoring system 506 may, at step 510, determine whether the visitor in an authorized visitor. To do so, RTLS may determine whether a signal was detected, such as from a badge of the visitor, as shown at step 509, indicating an authorized person has entered the room of the patient. If a signal is detected, the computerized patient monitoring system 506 continues monitoring. If no signal is detected, computerized patient monitoring system 506 may communicate an image of the visitor to central communication system 512. Central communication system 512 may be configured to send an alert of the unauthorized visitor to one or more designated recipients (e.g., caregiver(s) 520). Central communication system 512 may be an integral part of computerized patient monitoring system 506 and/or may be implemented using separate software, firmware, and/or hardware, possibly physically remote from central communication system 512. When an alert is triggered, the alert may be sent, at least initially, to the patient 502 being monitored, to give the patient 502 being monitored an opportunity to respond before alerting the central video monitoring system 516 and/or caregiver(s) 520. For example, an audible message may be played in the room where patient 502 is being monitored, possibly asking the visitor: "Please show your identification."

Shown as step 514 in FIG. 5, computerized patient monitoring system 506 can analyze subsequent image data from 3D motion sensor 504 for corrective action such as the unauthorized visitor adequately providing identification, such as by showing identifying or providing an indication consistent with a yes or no answer to determine if the action will be corrected. If 3D motion sensor 504 is equipped with microphones, computerized patient monitoring system 506 can analyze sound data for recognizable words, such as okay, yes, or no, help.

Central video monitoring system 516 may be alerted if no response is received at step 514, or if the response is unintelligible or indicates that the unauthorized visitor does not intend to comply. Alternately, or additionally, central video monitoring system 516 may be alerted with or even before patient 502, so that central video monitoring system 516 can determine whether the unauthorized visitor detected is, in fact, problematic. On receiving an alert, the central video monitoring system 516, or an attendant there, may view live image, video, and/or audio feed from the 3D motion sensor 504, and evaluate whether the unauthorized visitor presents a danger to the patient and/or himself. If patient 502 has been alerted by the central communication system 512, central video monitoring system 516 or an attendant there can use the data from 3D motion sensor 504 to evaluate whether a response from patient 502 indicates that the unauthorized visitor is complying with identification requirements. Central video monitoring system 516 and/or computerized patient monitoring system 506 may analyze the response from patient 502 and/or the unauthorized visitor, however, if the response does not include words or gestures recognizable by the computerized system, an attendant at central video monitoring system 516 may be able to interpret the person's response. If needed, the central video monitoring system 516 and/or the attendant could then approve alert(s) to appropriate caregiver(s) 520 and/or call for emergency assistance (e.g., send a request for security).

One or more caregiver(s) 520 local to patient 502 can be alerted with or even before patient 502 and/or central video monitoring system 516, so that the caregiver(s) 520 can assess what is happening in person. Or, monitored patient 502, caregiver(s) 520, and the central video monitoring system 516 could all be alerted at the same time. The priority and timing of alerts to different individuals or stations can be configured in accordance with the needs and desires of a particular facility, experience with a particular monitored individual or type of patient, or any other criterion of the system owner or user. This is true for initial alerts as well as continuing alerts (e.g., if an unauthorized visitor is detected, and no response is received or observed) or repeated alerts (two or more distinct events where an unauthorized visitor is detected). The priority and timing of alerts to different individuals may be different for initial, continuing, and/or repeated alerts.

Data associated with alerts may be logged by computerized patient monitoring system 506 and/or central video monitoring system 516 in a database 518. Data associated with an alert may include, without limitation, the telemetry data from 3D motion sensor 504 that triggered the alert; buffered data preceding the telemetry data that triggered the alert; telemetry data subsequent to the alert; the number and substantive content of an alert; the individual(s) and/or groups to whom an alert was addressed; the response, if any, received or observed following an alert; and combinations thereof. In embodiments, the database 518 also stores information regarding authorized visitors and information (e.g., RFID transmitter identification).

Figure 6:
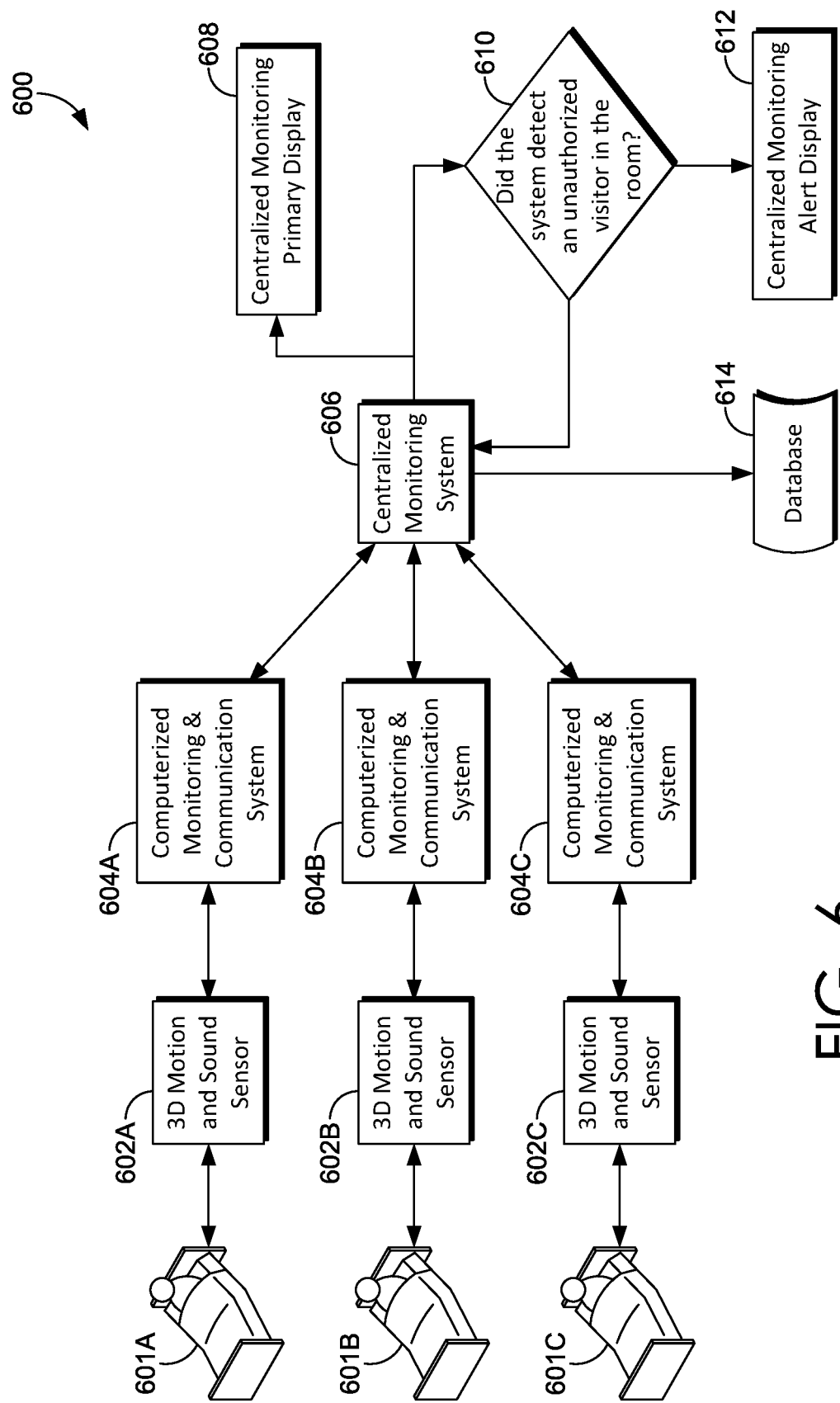

As shown in FIG. 6, centralized monitoring system 606 may receive data from multiple computerized monitoring and communication systems 604A, 604B, 604C. For simplicity, the computerized communication system associated with each computerized monitoring system is shown as an integrated component of the computerized monitoring system. If desired, separate computerized communication systems and/or a shared computerized communication system could be used. Computerized monitoring and communication systems 604 receive data from 3D motion sensors 602A, 602B, 602C, which are, respectively, monitoring persons 601A, 601B, 601C. Data received by the centralized monitoring system 606 from computerized monitoring and communication systems 604A, 604B, 604C may routinely be displayed on centralized monitoring primary display 608. A single primary display 608 may display data from more than computerized monitoring and communication systems 604A, 604B, 604C, shown as view 700 in FIG. 7. Alternately, primary display 608 may comprise two or more distinct screens, each of which may display data from one or more computerized monitoring systems. As shown, the display for monitored person 701C has an open configuration window 710, which is described in greater detail below.

When the centralized monitoring system 606 receives an alert from any of the computerized monitoring and communication systems 604A, 604B, 604C, indicating that a monitored person 601A, 601B, 601C is in proximity to an unauthorized visitor, audio and/or alert information for that particular person and/or the unauthorized visitor may be displayed on the centralized monitoring alert display 612. An alert can be presented in a variety of formats. An alert may be a visual cue on screen at the centralized monitoring system 606, such as the specific camera view flashing or being highlighted in a color to draw attention to that display among others. An alert may be an audible sound (e.g., a voice or alarm type sound) at the centralized monitoring system 606, an audible sound at the computerized monitoring and communication system attached to the 3D motion sensor, a text message, an email, turning on a light, or even running a program on a computer. Should the central monitoring station 150 receive alerts from more than one of the computerized monitoring and communication systems 604A, 604B, 604C, indicating that a person 601A, 601B, 601C is in proximity to an unauthorized visitor, the centralized monitoring alert display 612 may display the video, audio, and/or alerting information from all such instances at the same time. If no alert is received by the centralized monitoring station 606, it may be that nothing is displayed on the centralized monitoring alert display 612. Preferably, all monitored individual rooms can be displayed and visible on the centralized monitoring primary display 608 whether alerting or not. When an alert is generated, attention can be drawn to the particular camera on centralized monitoring primary display 608 and/or a duplicative display of the alerting camera can be displayed on a second separate computer monitor, e.g., the centralized monitoring alert display 612.

An electronic record of any alerts received, any responses to the alert observed or received, and/or any actions taken by the centralized monitoring system 606 can be stored in a database 614.

Figure 7:
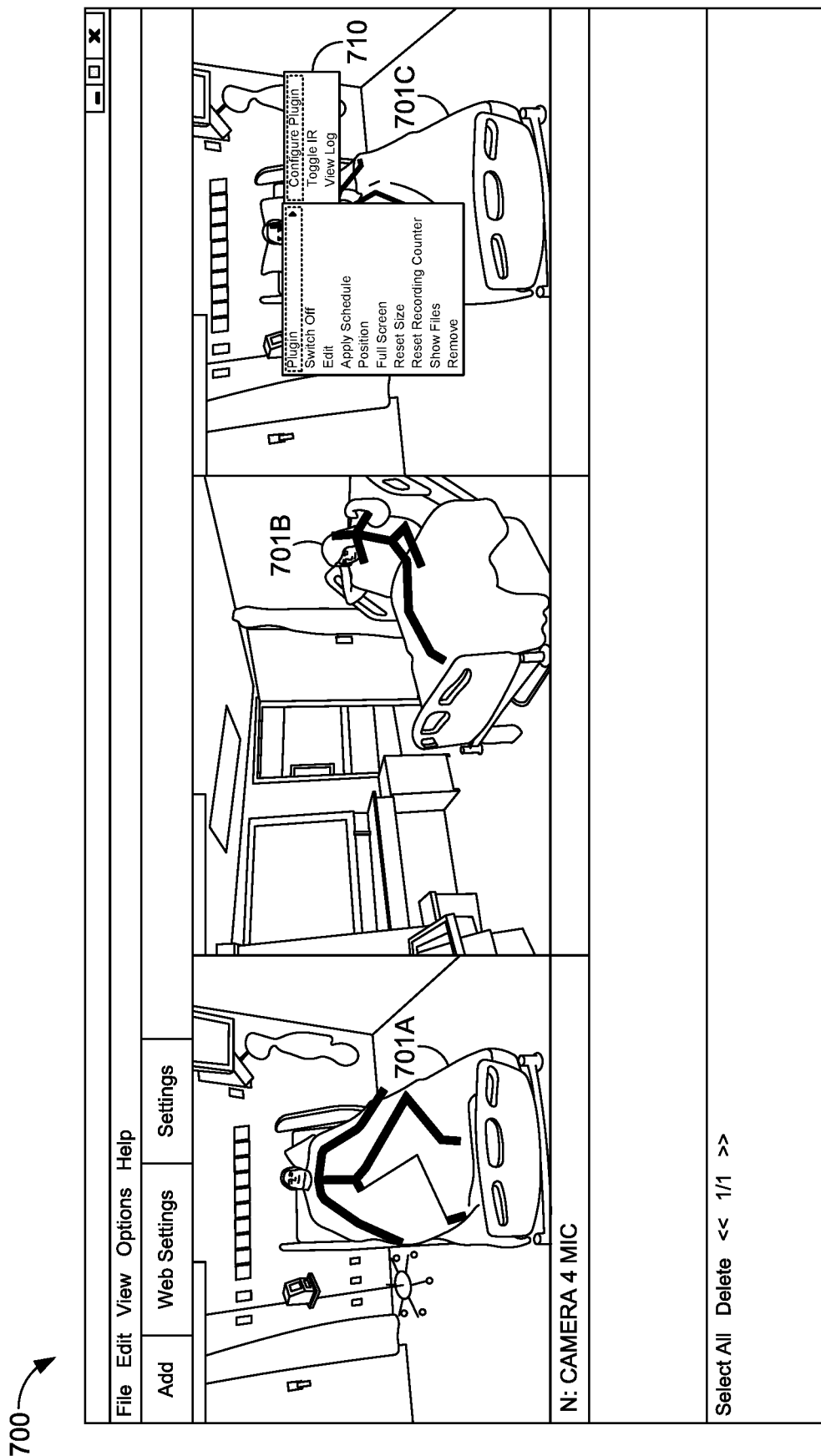
Figure 8:
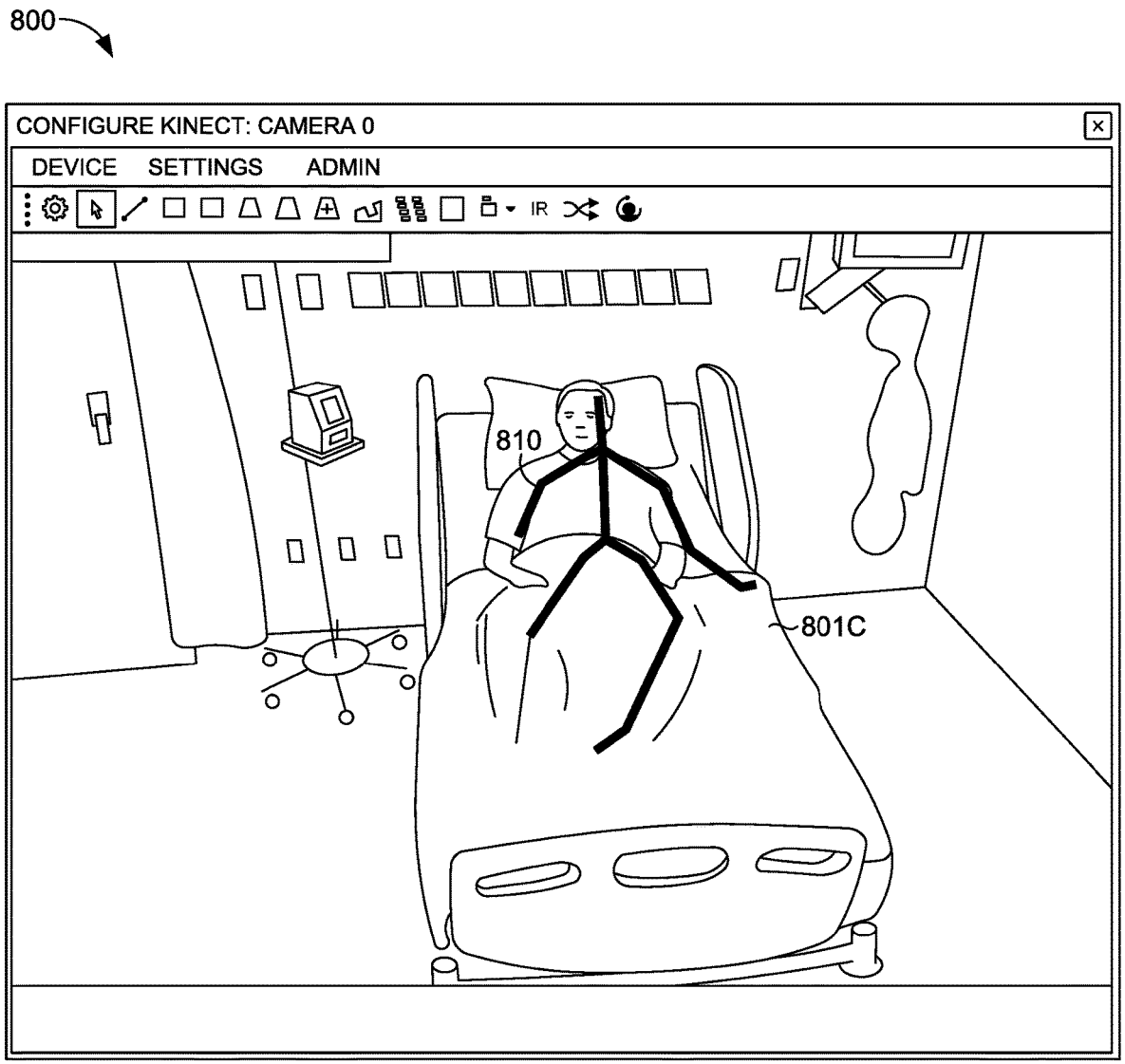
Figure 9:
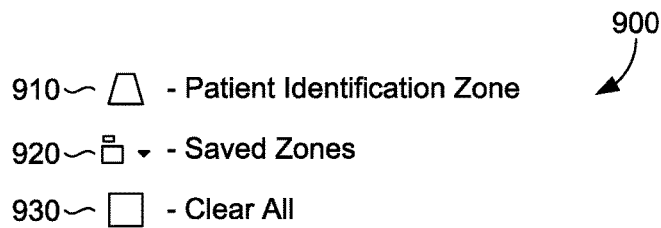

FIG. 7 shows an exemplary view for central monitoring primary display 700, including video data for multiple monitored persons 701A, 701B, and 701C displayed on a single screen. FIG. 8 shows an alternative view for central monitoring primary display 800, including image data for only monitored patient 801C. The view includes a skeletal FIG. 810, which may be identified by the central video monitoring system and used to track or "lock on to" the patient 801C. A skeletal FIG. 810 is shown in FIG. 8, however, alternate image analysis could be used, including, without limitation, blob recognition. No patient identification zones are marked in the image of FIG. 8. FIG. 9 shows an exemplary configuration menu 900, with an option 910 for configuring a face monitoring zone, an option 920 for configuring other saved zones, and an option 930 to clear all configured zones.

Figure 10:
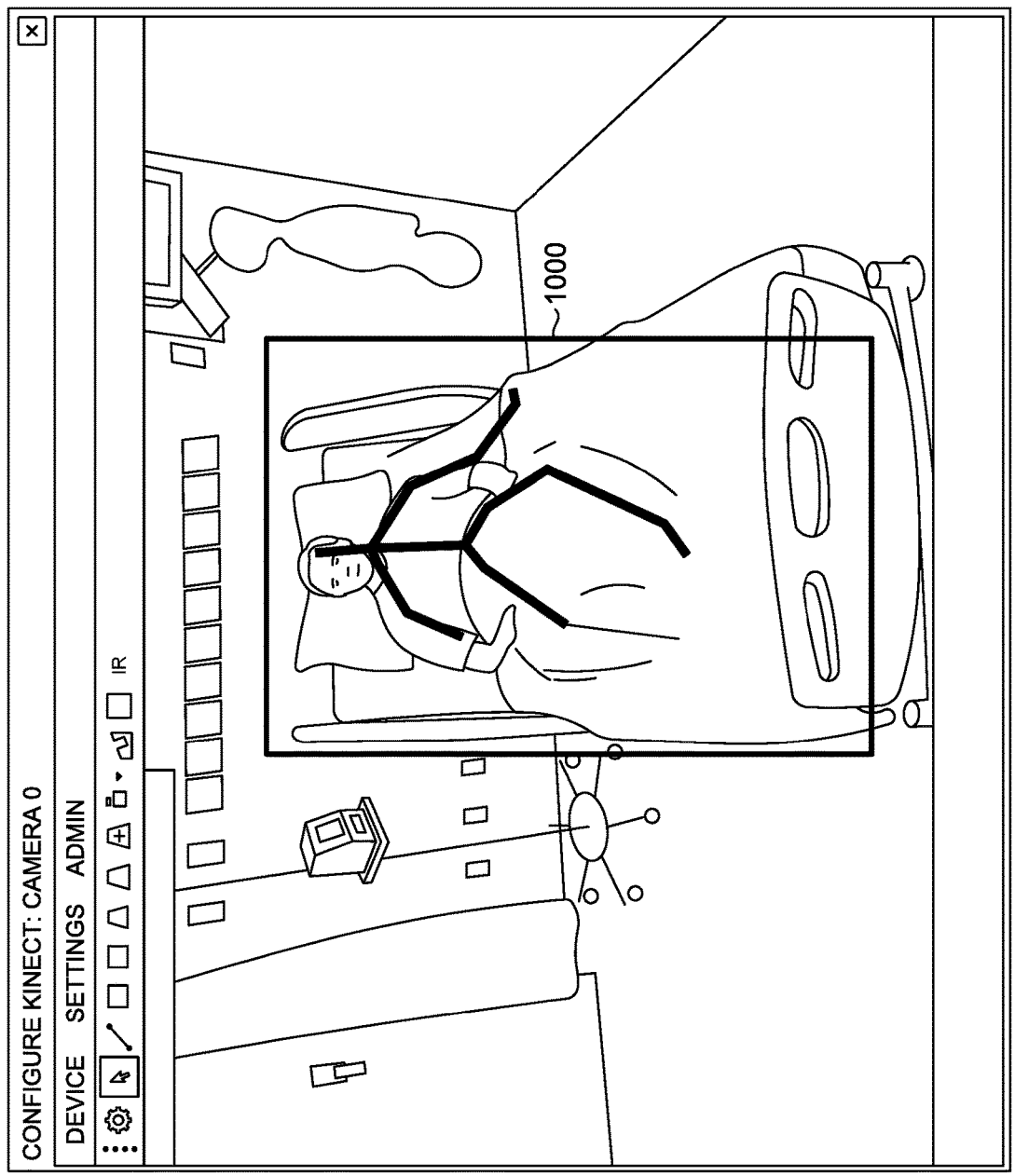

FIG. 10 shows a display view as it might appear on selecting a menu option to configure one or more zones. FIG. 10 shows a patient identification zone 1000 generally about the upper torso, shoulders, and head of a patient lying in a hospital bed. Patient identification zone 1000 may be configured by the computerized patient monitoring system. For example, patient identification zone 1000 may be defined as a fixed perimeter or volume around the head of a patient, as determined based on analysis using skeletal tracking, blob recognition, and/or facial tracking. If configured by the computerized patient monitoring system 106, a user may be allowed to modify the system-configured patient identification zone 1000, or a user may be required or allowed to manually configure the patient identification zone 1000. The 3D motion sensor 104 may collect image and/or sound data for a broader portion of a room than just the patient identification zone 1000. The computerized patient monitoring system 106 may analyze only data related to the patient identification zone 1000, with or without capturing images and/or sound from a broader portion of the room. This may reduce total processing capacity required, as the most processing-intensive algorithms (e.g., facial tracking, identification and tracking of reference points) are run on a limited data set. Capturing broader image data may help provide context for an alert, e.g., at central video monitoring system. For example, using image data from most or all of the room, central video monitoring system or an attendant there may determine that it is unnecessary to send an alert to a caregiver if there is already a caregiver in the room and tending to the patient being monitored at the time of an alert. A patient identification zone 1000 may also help the monitoring system "lock on" to a person and help avoid situations where a patient who is very close to the person being monitored might be tracked after moving away from the person. If the patient moves out of patient identification zone 1000, but the person being monitored does not leave patient identification zone 1000, the monitoring system will continue to monitor the person in patient identification zone 1000.

Using facial recognition algorithms, the computerized patient monitoring system may identify key features of the face of the patient being monitored. Key features may include, without limitation, the orbit of the eye socket(s), eyebrow(s), eyebrow ridge(s), the nose, the bridge of the nose, the mouth, top of the head, hairline, chin, ears, cheekbones, etc. The features used may vary with the kind of technology (e.g., visible vs. infrared light) and/or the prominent or accessible features on the patient.

The computerized patient monitoring system may use facial tracking rather than facial recognition, facial recognition implying that the software attempts to identify a particular person (e.g., Jane Doe) based on facial features, as opposed to recognizing a particular facial feature (e.g., an eye) using facial tracking. If desired, facial recognition algorithms could also be used, e.g., to confirm that the system has "locked on" to the intended person being monitored, or to confirm the identity of the person.

The computerized patient monitoring system may identify soft-tissue reference points on the face of the monitored person. Exemplary soft-tissue reference points may generally outline the eyes and/or the mouth. Other exemplary soft-tissue reference points, which could be used with or in lieu of the eyes and/or mouth, include the jowls, flesh along the cheekbone, the neck, and the portion of the neck immediately under the chin. The eyes and/or mouth may be preferred as they are easily identified by facial tracking algorithms and tend to be readily visible even if the person being monitored is wearing a blanket or high-necked clothing.

Figure 11:
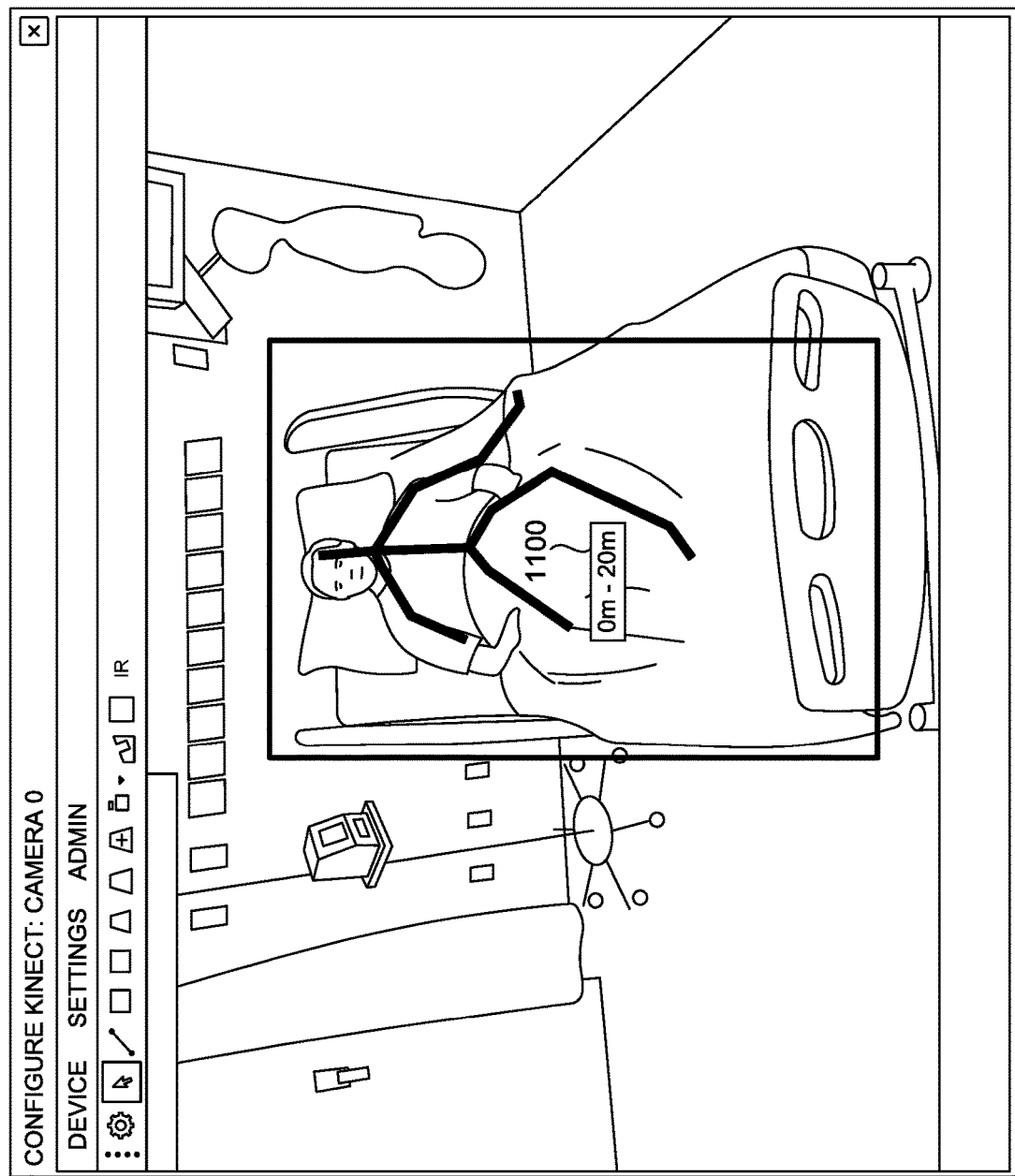

If patient identification zone 1000 is configured by a user, the user may operate an input device to select a point on an image or video from the computerized patient monitoring station. The user may draw a perimeter defining a zone freehand, or may drag the input device (such as an electronic stylus or mouse pointer) from one point to another to define a diagonal axis for the perimeter of the zone. Other configuration options, including drag-and-drop templates and coordinate identification, could be used. A 2D monitoring zone can be operated as a perimeter, or a third dimension of depth can be specified. As with the perimeter, the computerized patient monitoring system can define or recommend a depth measurement, such as shown by label 1100 in FIG. 11, or the user can provide the depth measurement, as described below.

Figure 12:
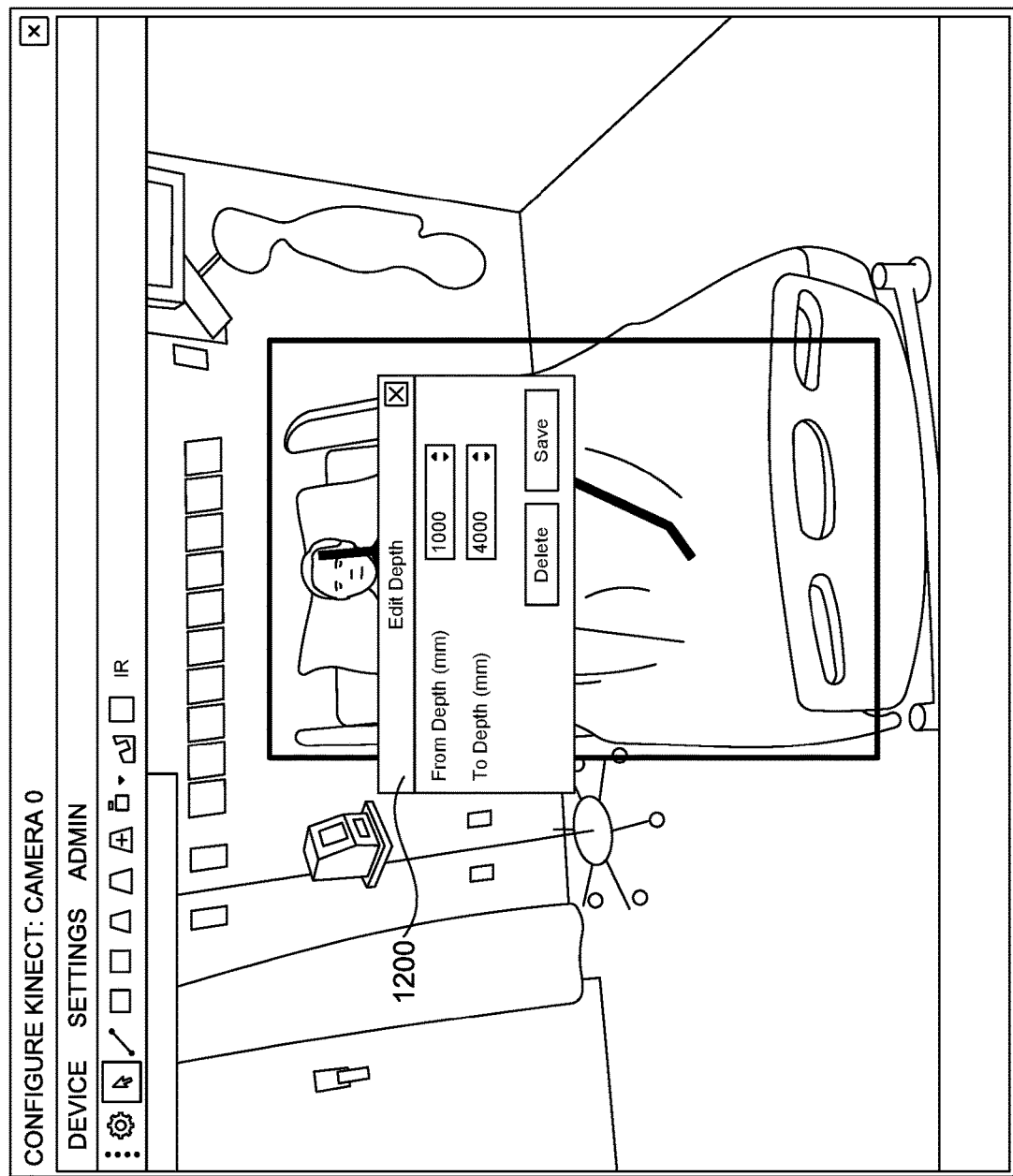

FIG. 12 shows a pop-up menu 1200 allowing a user to configure or reconfigure the depth of a patient identification zone. The exemplary pop-up menu 1200 solicits a depth parameter specified in millimeters (mm), however, any desired unit of measure could be used, including, without limitation, centimeters (cm), meters (m), inches, feet, and yards.

Figure 13:
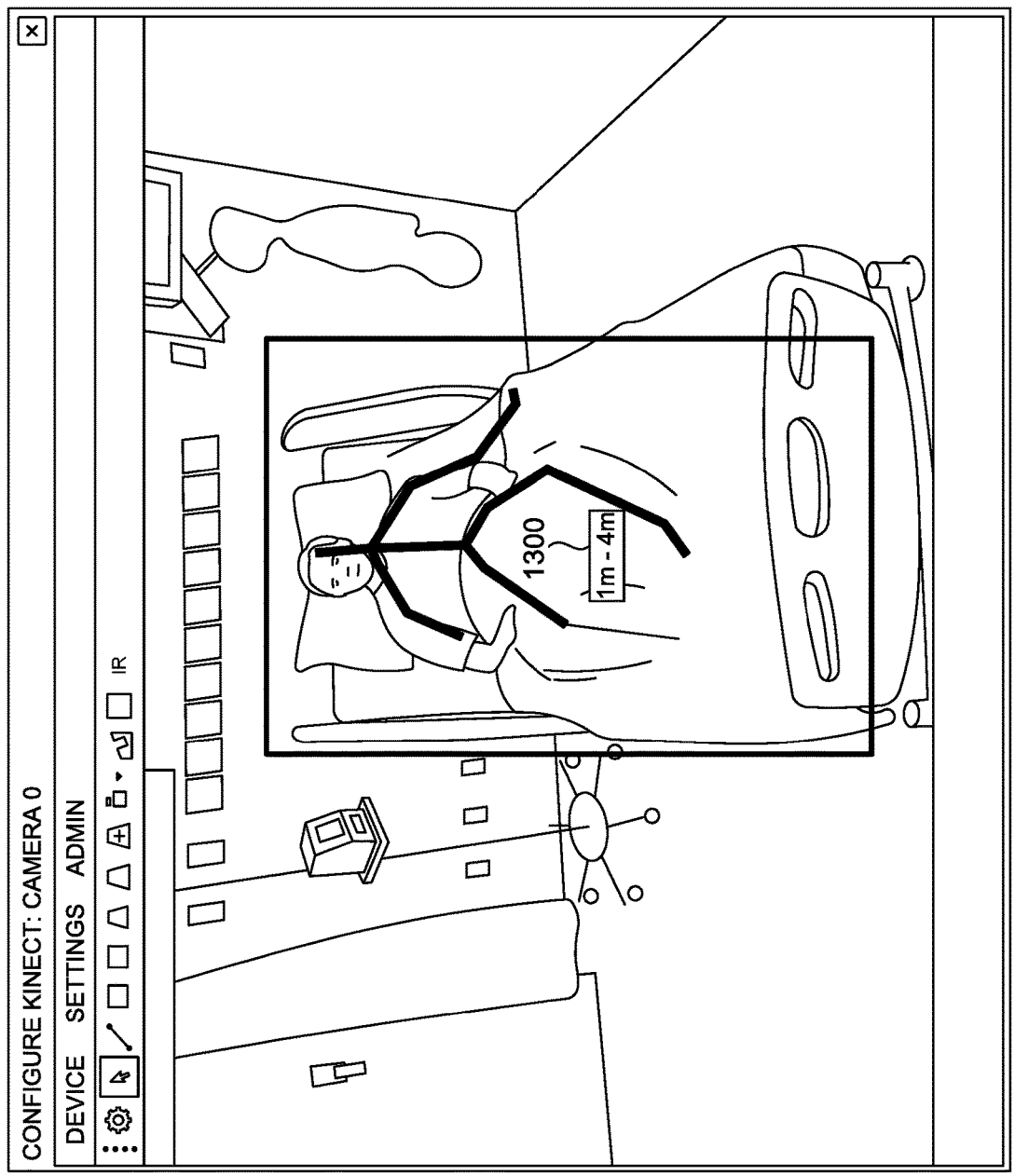

On setting a depth parameter, and while still in a configuration view, the depth of the patient identification zone may be visible as a label 1300, as shown in FIG. 13. The depth label 1300 may not be visible during routine monitoring and/or alert monitoring, so as not to obscure the person being monitored and/or other activity in any image data from the 3D motion sensor.

Figure 14:
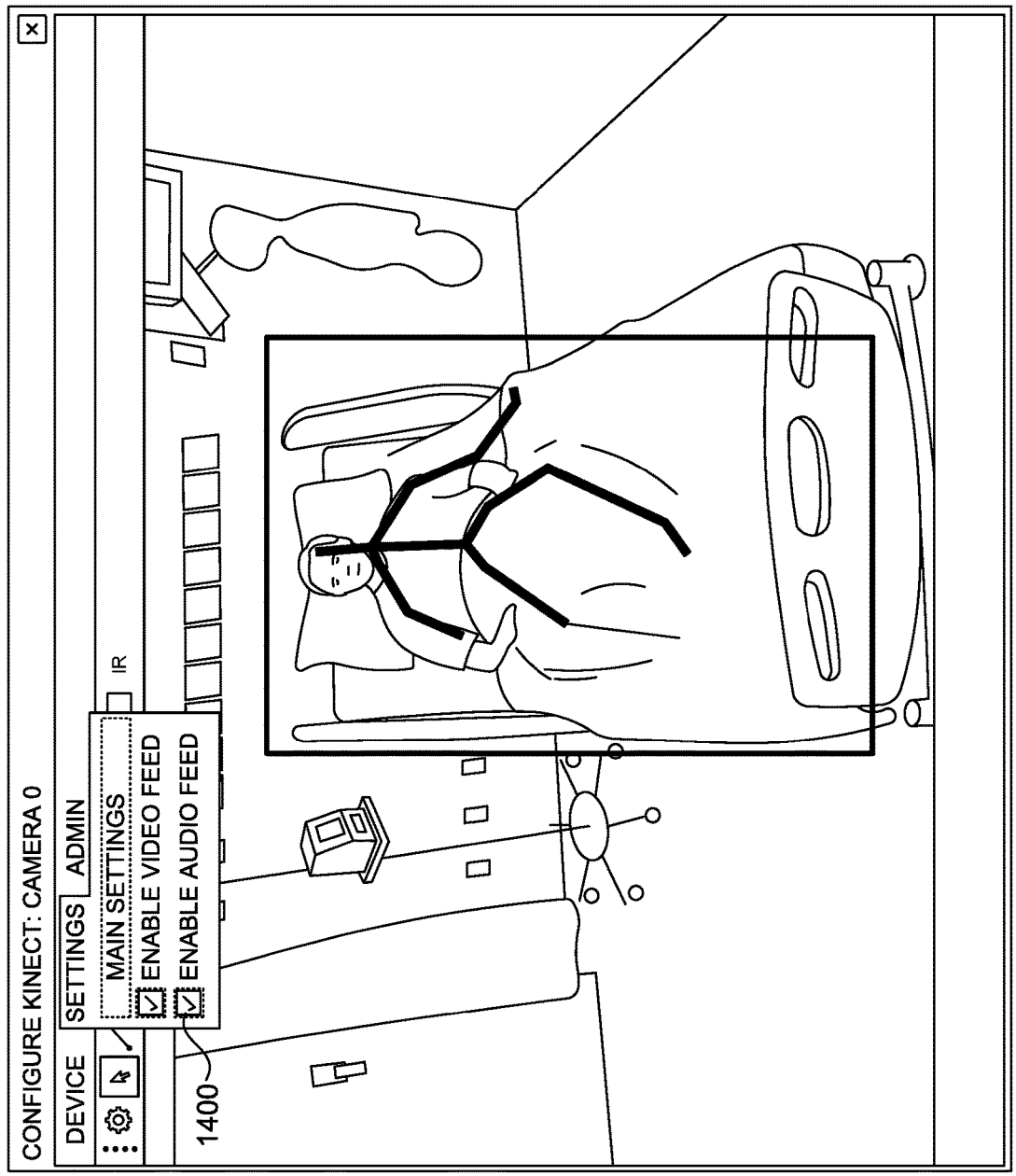

FIG. 14 shows another menu 1400 from a configuration view that may be displayed to a user. As shown in FIG. 14, a user may be permitted to turn monitoring on or off (e.g., by "unchecking" both video feed and audio feed), or to turn off video feed only, or to turn off audio feed only, if audio feed is available. It may be desirable to disable audio feed, for example, at central video monitoring system, to prevent overlapping audio feeds from becoming unintelligible noise. If voice or word recognition algorithms are used, those algorithms may run at computerized patient monitoring system even if audio feed is disabled at a monitoring station, such as central video monitoring system. On alert or as desired, the audio feed could be enabled for one or more particular persons being monitored, e.g., to provide context for an alert. It may be desirable to disable audio and/or video feed to provide some privacy to the patient corresponding to the person being monitored. For example, it may be desirable to disable audio and/or video feed while the patient is being examined by a medical professional, or bathed, or while visitors are present. The need for computerized monitoring is somewhat reduced while the patient is interacting with medical professionals, caregivers, or visitors. However, if desired, the audio and/or video feed can be maintained even when there are other others with the patient corresponding to the person being monitored.

Although patient identification zone may be configured and operational, the zone parameters, depicted in FIG. 14, may not be displayed outside of the configuration screens. In other words, the zone may be configured and operational but may not be not superimposed on the images of patient, so as to permit an unobstructed view of patient (e.g., at central video monitoring system or while configuring other aspects of the monitoring system).

Figure 15:
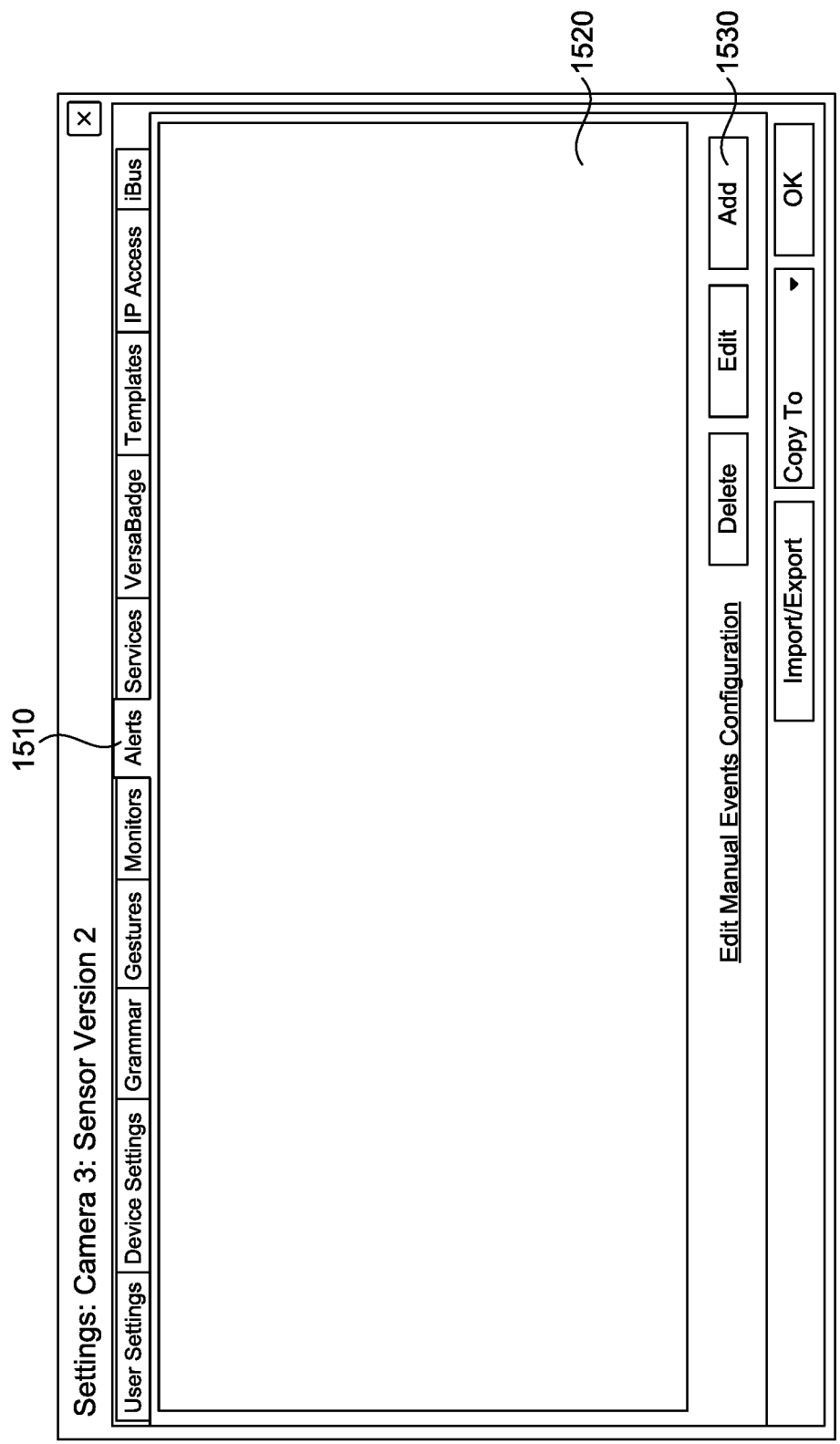

If the Device menu 1400 in FIG. 14 is selected, the user may see a pop-up menu as shown in FIG. 15. The use of pop-up, drop down, tabular, or other kinds of menus may be recommended based on, for example, the number and kinds of options associated with a particular menu. However, different kinds of menus could be presented based on user or facility preferences. Pop-up menu includes a number of tabs, from which a tab for Alerts 1510 has been selected in FIG. 15. The space within the Alerts window 1520 is blank, indicating that no alerts have been configured. If a user selects Add button 1530 at the bottom of the Alerts tab 1510, a new pop-up menu 1620 may appear, as shown in FIG. 16.

Figure 16:
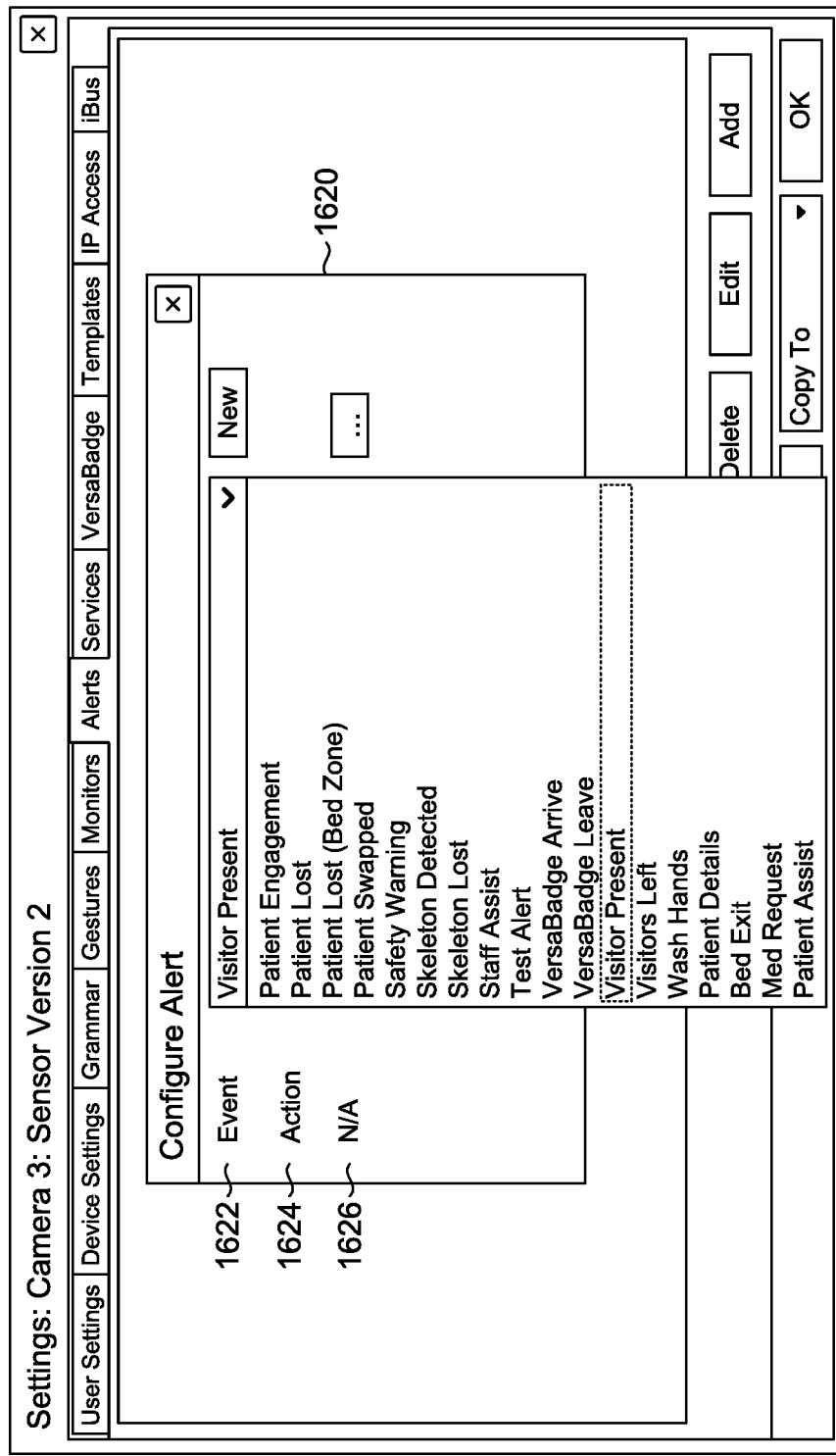

As shown in FIG. 16, pop-up menu 1620 further includes drop-down menus to configure an alert by specifying an event 1622, an action 1624, and, if applicable, an N/A field 1626. As with the kinds of menus, the particular words used to describe an event, action, and/or N/A field may be modified to reflect the environment in which the system is being used, or the facility or personnel using the system, or a particular station. For example, a system, station, or user interface may be configured for use in a hospital using clinical terminology. As another example, a remote central video monitoring system may have an attendant who is not a medical professional, and lay terminology might be used in lieu of or in addition to clinical terminology. Family or other non-professional and/or non-medical caregivers may have access to the monitoring system and/or serve as an attendant for a remote monitoring station, and the menus for those users may similarly use descriptive, non-clinical terminology in addition to or in lieu of clinical terminology. Different languages could also be used for different interfaces. As shown in FIG. 16, the monitoring system may include monitoring and/or alert functions unrelated to unauthorized visitors, as well as the "Visitor Present" option presented. If desired, other options may be removed from the drop-down menu to simplify user configuration choices for users who do not want or need access to the other functions. Changes to the menus, including changes to the range of menu options and the terminology used in the menus, may be configured when the system is installed or when access is provided to a specific user, and may not require or may not be available for further modification by routine system users.

Figure 17:
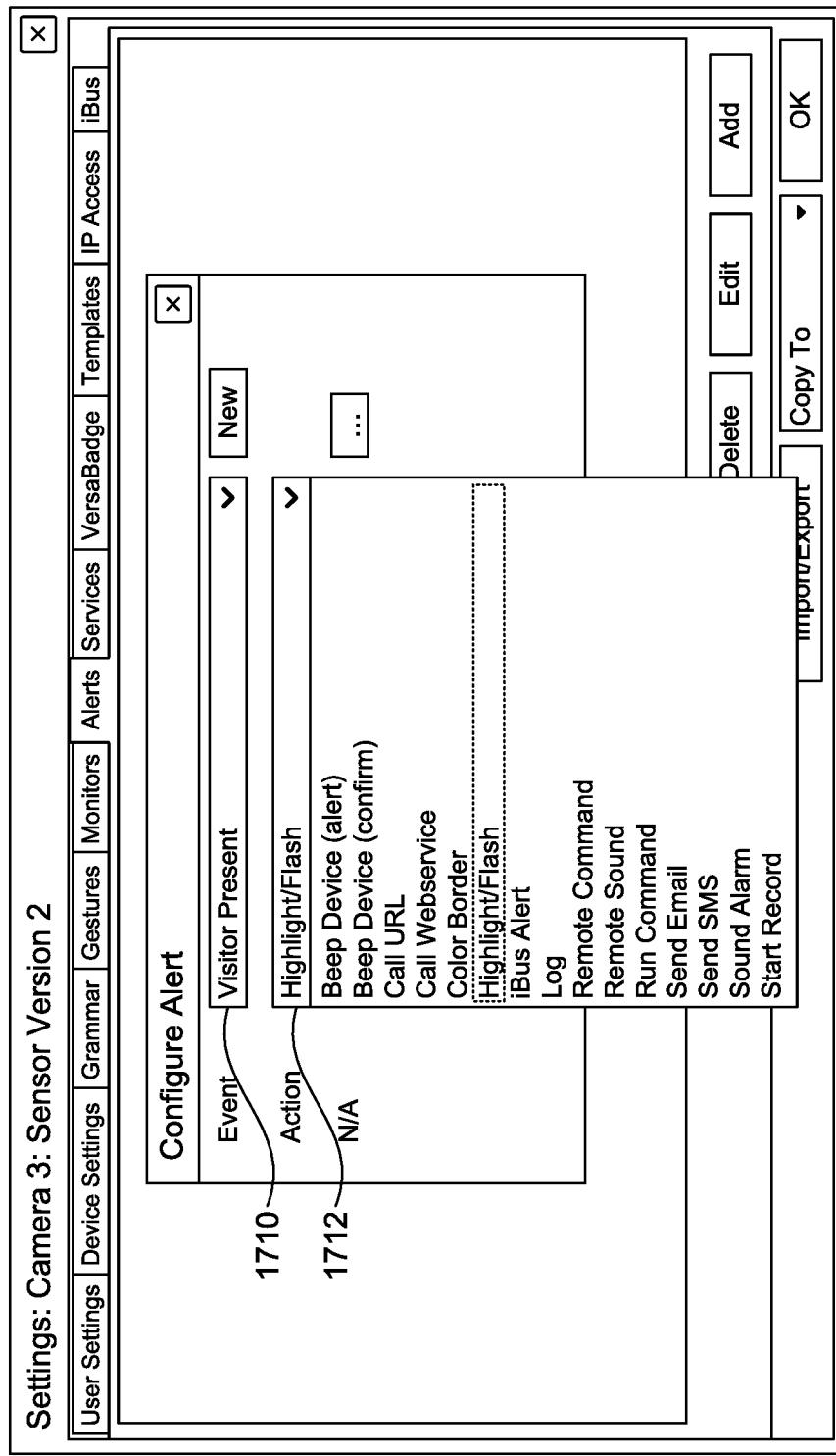

On selection of an event 1622 in FIG. 16, the user may be able to select an action 1624, as shown in FIG. 17. Several of the options relate to alerts, e.g., to provide different audible signals to the 3D motion sensor and/or computerized patient monitoring system; to add or change a color border to a display of image data; to highlight or flash a display of image data; to log an alert, as in database; to send e-mail or SMS; or to provide other alerts. As shown in FIG. 17, the user has elected to highlight/flash 1712 a display of image data if event 1710 occurs, e.g., if a visitor is present.

Figure 18:
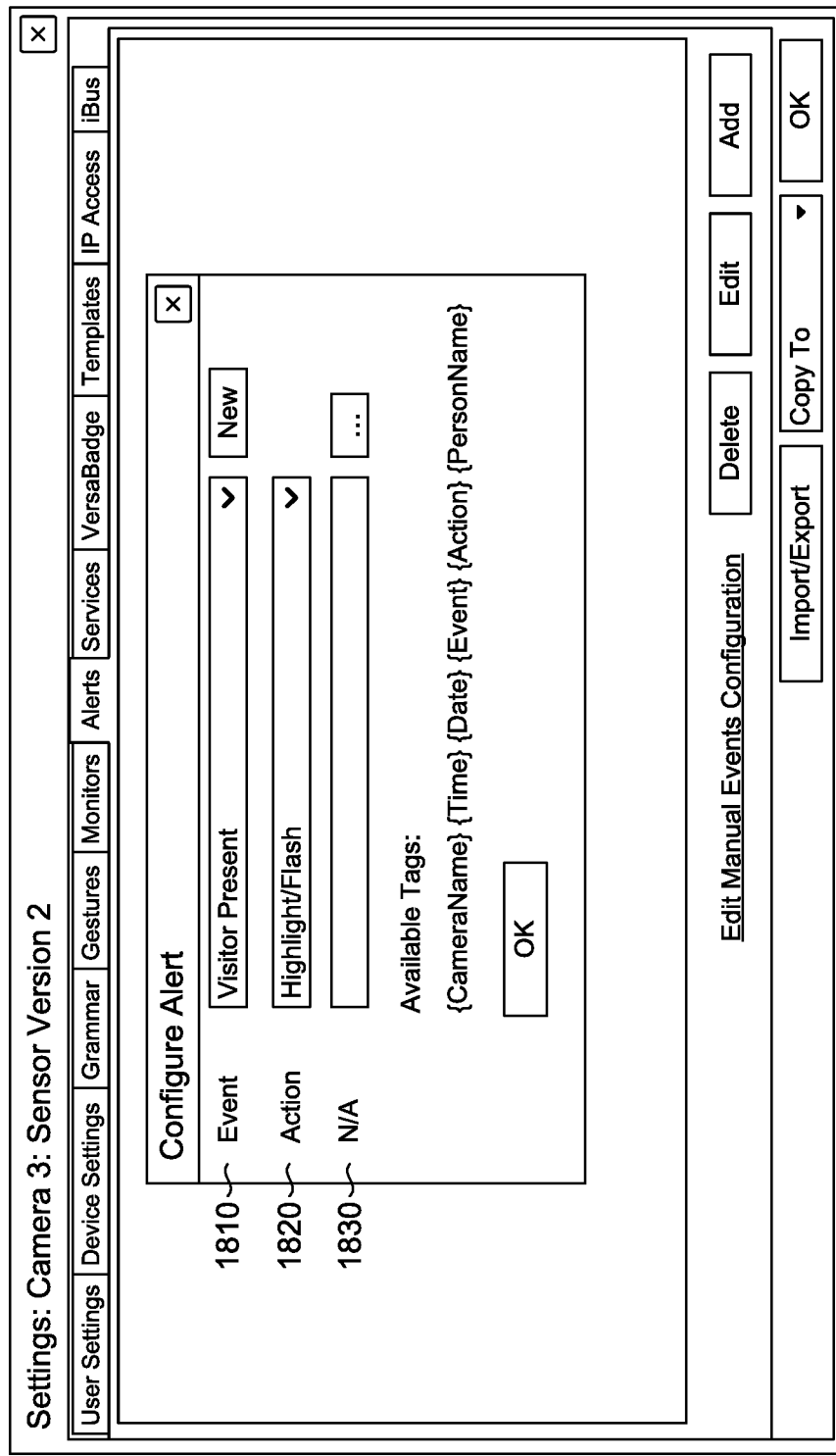

As shown in FIG. 18, N/A field 1830 may be blank and/or inactive depending upon the event 1810 and action 1820 selected. In the example shown in FIG. 17, the option to highlight/flash an image display does not require further configuration, and so N/A field 1830 is blank and inactive, in that the user cannot input options for N/A field 1830. However, if the action was set to send an alert, for example, N/A field 1830 might become active and allow a user to designate a recipient and/or recipient group to whom the alert should be sent. If the user desires to send different kinds of alerts to different recipients or groups of recipients, multiple alerts could be configured, with each alert specifying a different action 1820 (e.g., send e-mail vs. send SMS) and/or a different recipient. As another example, the N/A field 1830 could be used to specify where to log the occurrence of an event, for example, if more than one database is available to the monitoring system, or if data for more than one monitored person is stored in the available database(s).

Figure 19:
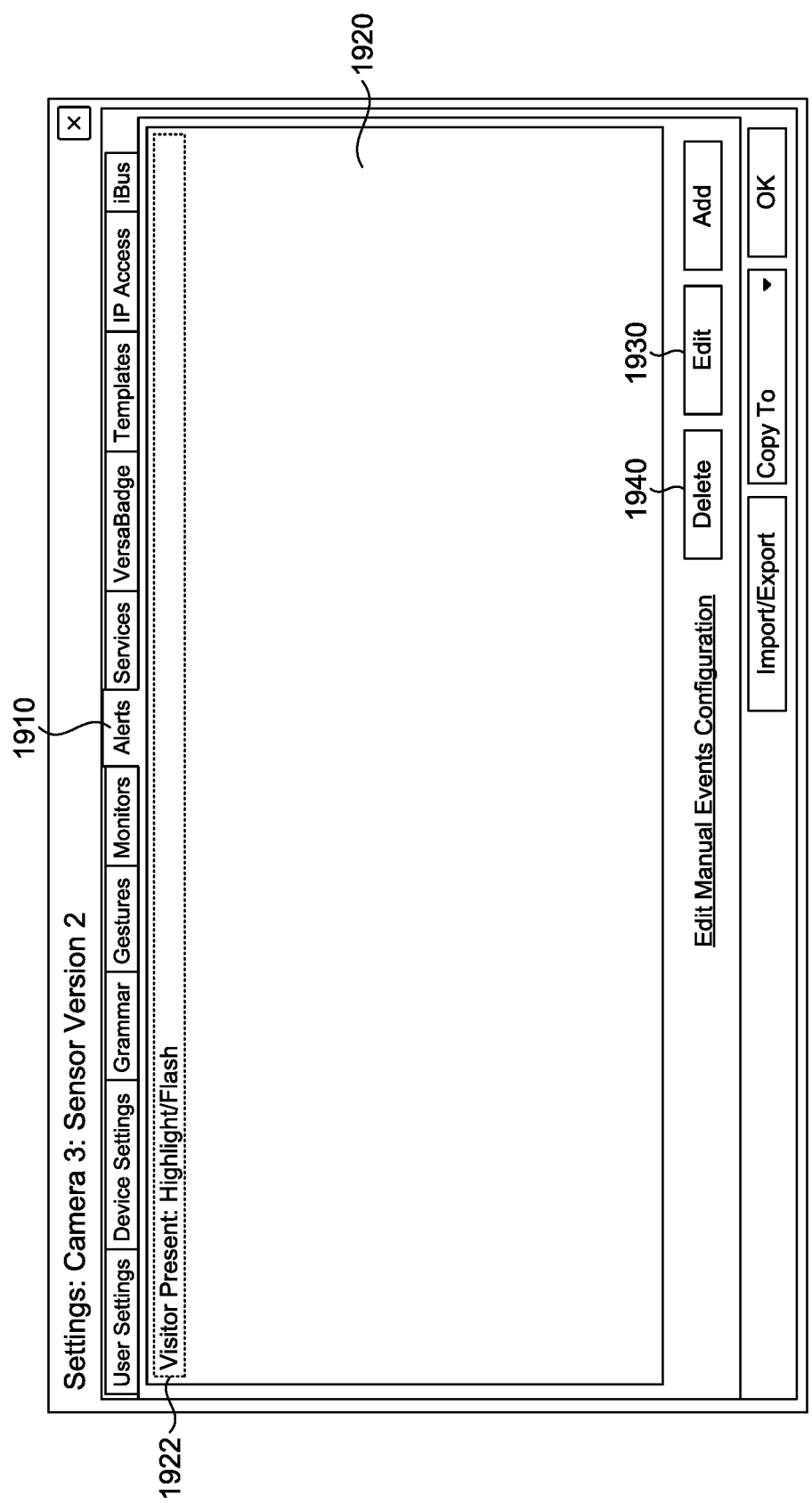

As shown in FIG. 19, after an alert has been configured, the configuration view may revert to alert tab 1910, now showing a brief description of configured alert 1922 in alerts window 1920. If additional alerts were configured, alerts window 1920 might display a selectable list of configured alerts, including configured alert 1922. Once configured, alerts may be edited or deleted using buttons 1930 or 1940, respectively. Edit button 1930 may re-open the configuration view shown in FIGS. 16-18, with the drop-down menus open to receive alternate selections.

FIG. 20 shows a view 2000 of image data from multiple 3D motion sensors monitoring persons 2010A, 2010B, and 2010C, as might appear on a central monitor primary display. The configuration window has been closed, providing an unobstructed view of monitored patients. Depending upon the configuration for primary display, each panel 2020, 2030, and 2040 may display live video, intermittent images (e.g., "still" shots from a video data feed) and/or audio data for monitored persons 2010A, 2010B, and 2010C, respectively.

The various computerized systems and processors as described herein may include, individually or collectively, and without limitation, a processing unit, internal system memory, and a suitable system bus for coupling various system components, including database 118, with a control server. Computerized patient monitoring system 106 and/or central video monitoring system 116 may provide control server structure and/or function. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

The computerized systems typically include therein, or have access to, a variety of computer-readable media, for instance, database 118. Computer-readable media can be any available media that may be accessed by the computerized system, and includes volatile and nonvolatile media, as well as removable and non-removable media. By way of example, and not limitation, computer-readable media may include computer-storage media and communication media. Computer-readable storage media may include, without limitation, volatile and nonvolatile media, as well as removable and non-removable media implemented in any method or technology for storage of information, such as computer readable instructions, data structures, program modules, or other data. In this regard, computer-storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server. Computer-readable storage media excludes signals per se.

Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media. The computer-readable storage media discussed above, including database 118, provide storage of computer readable instructions, data structures, program modules, and other data for the computerized systems. Computer readable instructions embodied on computer-readable storage media may be accessible by unauthorized visitor system 100 and/or component(s) thereof, and, when executed by a computer processor and/or server, may cause the system to function and/or perform the methods described herein.

The computerized systems may operate in a computer network using logical connections to one or more remote computers. Remote computers may be located at a variety of locations, for example, but not limited to, hospitals and other inpatient settings, veterinary environments, ambulatory settings, medical billing and financial offices, hospital administration settings, home health care environments, payer offices (e.g., insurance companies), home health care agencies, clinicians' offices and the clinician's home or the patient's own home or over the Internet. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers may also be physically located in non-traditional medical care environments so that the entire health care community may be capable of integration on the network. The remote computers may be personal computers, servers, routers, network PCs, peer devices, other common network nodes, or the like, and may include some or all of the elements described above in relation to the control server. The devices can be personal digital assistants or other like devices.

Exemplary computer networks may include, without limitation, local area networks (LANs) and/or wide area networks (WANs). Such networking environments are commonplace in offices, enterprise-wide computer networks, intranets, and the Internet. When utilized in a WAN networking environment, the control server may include a modem or other means for establishing communications over the WAN, such as the Internet. In a networked environment, program modules or portions thereof may be stored in the control server, in the database 118, or on any of the remote computers. For example, and not by way of limitation, various application programs may reside on the memory associated with any one or more of the remote computers. It will be appreciated by those of ordinary skill in the art that the network connections shown are exemplary and other means of establishing a communications link between the computers may be utilized.

In operation, a user may enter commands and information into the computerized system(s) using input devices, such as a keyboard, a pointing device (commonly referred to as a mouse), a trackball, a touch pad, a 3D Gesture recognition camera or motion sensor. Other input devices may include, without limitation, microphones, satellite dishes, scanners, or the like. In addition to or in lieu of a monitor, the computerized systems may include other peripheral output devices, such as speakers and a printer.

Many other internal components of the computerized system hardware are not shown because such components and their interconnection are well known. Accordingly, additional details concerning the internal construction of the computers that make up the computerized systems are not further disclosed herein.

Methods and systems of embodiments of the present disclosure may be implemented in a WINDOWS or LINUX operating system, operating in conjunction with an Internet-based delivery system, however, one of ordinary skill in the art will recognize that the described methods and systems can be implemented in any operating system suitable for supporting the disclosed processing and communications. As contemplated by the language above, the methods and systems of embodiments of the present invention may also be implemented on a stand-alone desktop, personal computer, cellular phone, smart phone, tablet computer, PDA, or any other computing device used in a healthcare environment or any of a number of other locations.

From the foregoing, it will be seen that this disclosure is well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

What is claimed is:

1. A system for detecting unauthorized visitors, the system comprising:
   one or more 3D motion sensors located to provide the one or more 3D motion sensors with a view of a person and surrounding area to be monitored; and
   a computerized monitoring system communicatively coupled to the one or more 3D motion sensors, the computerized monitoring system configured to:
   receive images of the area to be monitored from the one or more 3D motion sensors;
   detect when a visitor enters the view of the one or more 3D motion sensors;
   receive a plurality of registered reference points on faces of registered visitors from a remote database;
   assign a plurality of reference points on the face of the visitor in one or more images from the one or more 3D motion sensors by automatically assigning initial reference points on the face of the visitor and assigning one or more alternative reference points upon detecting of one or more bandages on the face of the visitor;
   determine whether the visitor is unauthorized or authorized by comparing the plurality of reference points on the face of the visitor and the plurality of registered reference points;
   initiate an alert being sent to one or more designated recipients; and
   responsive to a determination that the visitor is authorized suppressing the alert.

2. The system of claim 1 further comprising a central communication system communicatively coupled to the computerized monitoring system, wherein initiating the alert to one or more designated recipients comprises transmitting an indication that the unauthorized visitor was detected to the central communication system and wherein the central communication system sends the alert to the one or more designated recipients.

3. The system of claim 2, wherein the central communication system is located remotely from the computerized monitoring system.

4. The system of claim 1, wherein determining whether the visitor is an unauthorized visitor further comprises determining whether the visitor is registered.

5. The system of claim 4, wherein the visitor is determined to be an unauthorized visitor upon determining the visitor is not registered.

6. The system of claim 5, wherein the computerized monitoring system is further configured to create a recognition profile for the visitor upon determining the visitor is not registered.

7. The system of claim 1, wherein the computerized monitoring system is further configured to identify the person being monitored utilizing skeletal tracking or blob detection.

8. The system of claim 1, wherein determining whether the visitor is unauthorized or authorized comprises by comparing positions, distances between, sizes, or shapes of the reference points on the face of the visitor to positions, distances between, sizes, or shapes of the reference points of the plurality of registered reference points.

9. The system of claim 1, wherein the computerized monitoring system is further configured to determine that the visitor is a caregiver and suppressing the alert upon determining that the visitor is a caregiver.

10. The system of claim 1 further comprising:
    a central video monitoring system configured to display at least a portion of images captured by the one or more 3D motion sensors; and
    a central communication system that is integrated with the computerized monitoring system and is communicatively coupled to the central video monitoring system, wherein when it is determined that the visitor is an unauthorized visitor, the central communication system sends an alert to the central video monitoring system.

11. A computerized method for detecting unauthorized visitors, the method implemented by one or more processors and comprising:
    receiving, from one or more 3D motion sensors, an image of a visitor within an area to be monitored;
    receive a plurality of registered reference points on faces of registered visitors from a remote database;
    assigning a plurality of reference points on the face of the visitor in the image from the one or more 3D motion sensors by automatically assigning initial reference points on the face of the visitor and assigning one or more alternative reference points upon detecting of one or more bandages on the face of the visitor;
    determine whether the visitor is unauthorized or authorized by comparing the plurality of reference points on the face of the visitor and the plurality of registered reference points;
    initiating an alert being sent to one or more designated recipients; and
    responsive to a determination that the visitor is authorized suppressing the alert.

12. The computerized method of claim 11, further comprising establishing a virtual zone around an individual to be monitored within the area to be monitored.

13. The computerized method of claim 12, wherein the alert is initiated only upon determining the unauthorized visitor is within the virtual zone around the individual to be monitored.

14. The computerized method of claim 11, further comprising, upon determining the visitor is unauthorized, determining whether the visitor made one or more corrective actions after the alert is sent to one or more designed recipients.

15. The computerized method of claim 14, wherein the one or more corrective actions comprises moving away from an individual being monitored.

16. Non-transitory computer-readable storage media having embodied thereon instructions that, when executed by one or more computer processors, cause the one or more computer processors to:
    receive, from one or more 3D motion sensors, images of a visitor within an area having an individual to be monitored;
    assign a plurality of reference points on the face of the visitor in one or more images received from the one or more 3D motion sensors by automatically assigning initial reference points on the face of the visitor and assigning one or more alternative reference points upon detecting of one or more bandages on the face of the visitor;

receive a plurality of registered reference points on faces of registered visitors from a remote database;

determine whether the visitor is unauthorized or authorized by comparing the plurality of reference points on the face of the visitor and the plurality of registered reference points;

initiate an alert being sent to one or more designated recipients; and responsive to a determination that the visitor is authorized suppressing the alert.

17. The computer-readable storage media of claim 16, wherein one of the one or more designated recipients is a central video monitoring system comprising a primary display and an alert display, and wherein the central video monitoring system moves a display of at least a portion of the one or more images of the visitor from the primary display to the alert display.

18. The computer-readable storage media of claim 16, wherein the instructions further cause the one or more computer processors to determine whether the visitor is registered and, upon determining the visitor is not registered, create a profile for the visitor.

19. The computer-readable storage media of claim 16, wherein the visitor is determined to be an unauthorized visitor when the visitor is not identified as someone who is a registered visitor or when the visitor is registered and indicated as someone who is not permitted to be in close proximity to the individual being monitored.

20. The computer-readable storage media of claim 16, wherein the instructions further cause the one or more computer processors to identify the individual being monitored utilizing skeletal tracking or blob detection.

* * * * *

UNITED STATES PATENT AND TRADEMARK OFFICE
CERTIFICATE OF CORRECTION

| | |
|---|---|
| PATENT NO. | : 11,363,966 B2 |
| APPLICATION NO. | : 16/830498 |
| DATED | : June 21, 2022 |
| INVENTOR(S) | : Michael Kusens et al. |

It is certified that error appears in the above-identified patent and that said Letters Patent is hereby corrected as shown below:

In the Specification

Column 13, Line 32-33, Delete "skeletal FIG." and insert -- skeletal figure --.

Column 13, Line 35, Delete "skeletal FIG." and insert -- skeletal figure --.

Column 15, Line 37, Delete "may not be not" and insert -- may not be --.

Signed and Sealed this
Thirty-first Day of January, 2023

Katherine Kelly Vidal
*Director of the United States Patent and Trademark Office*